US007001644B2

(12) United States Patent
Baudin et al.

(10) Patent No.: US 7,001,644 B2
(45) Date of Patent: Feb. 21, 2006

(54) SURFACE-ACTIVE PHOTOINITIATORS

(75) Inventors: Gisèle Baudin, Allschwil (CH); Tunja Jung, Rheinfelden-Herten (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 55 days.

(21) Appl. No.: 10/450,228

(22) PCT Filed: Dec. 6, 2001

(86) PCT No.: PCT/EP01/14354

§ 371 (c)(1),
(2), (4) Date: Jun. 11, 2003

(87) PCT Pub. No.: WO02/48202

PCT Pub. Date: Jun. 20, 2002

(65) Prior Publication Data

US 2004/0034115 A1    Feb. 19, 2004

(30) Foreign Application Priority Data

Dec. 13, 2000    (EP) .................................. 00811184

(51) Int. Cl.
  $C08J\ 3/24$    (2006.01)
  $C08J\ 3/28$    (2006.01)
  $C08F\ 2/46$    (2006.01)
  $C08F\ 2/50$    (2006.01)

(52) U.S. Cl. ...................... 427/508; 428/558; 428/559; 428/385.5; 522/36; 522/42; 522/46; 522/173; 522/170; 522/174; 522/182; 522/150; 522/151; 522/153; 522/152

(58) Field of Classification Search ................ 522/33, 522/46, 42, 173, 170, 174, 150, 151, 152, 522/153, 182; 427/508, 558, 559, 385.5
See application file for complete search history.

(56) References Cited

U.S. PATENT DOCUMENTS

| | | | |
|---|---|---|---|
| 4,308,400 A | | 12/1981 | Felder et al. ............... 568/336 |
| 4,347,111 A | * | 8/1982 | Gehlhaus et al. ............... 522/8 |
| 4,351,708 A | * | 9/1982 | Berner et al. ................. 522/25 |
| 4,582,862 A | | 4/1986 | Berner et al. ................. 522/14 |
| 4,922,004 A | * | 5/1990 | Kohler et al. ............... 560/221 |
| 5,629,356 A | | 5/1997 | Desobry et al. ............. 522/34 |
| 6,022,906 A | | 2/2000 | Ohwa et al. ................... 522/8 |

FOREIGN PATENT DOCUMENTS

| | | |
|---|---|---|
| DE | 2722264 | 11/1978 |
| DE | 19753655 | 6/1998 |
| DE | 19907957 | 9/1999 |
| EP | 0003002 | 7/1979 |
| EP | 0844286 | 5/1998 |
| EP | 0898202 | 2/1999 |
| WO | 86/05778 | 10/1986 |
| WO | 98/00456 | 1/1998 |

OTHER PUBLICATIONS

English Abstr. for DE 19907957 (1999).
Patent Abstracts of Japan vol. 1996, No. 12, for JP 08211603 (1996).
Schultz et al., Journal of Polymer Science, Polymer Physics Edition, John Wiley and Sons, New York, vol. 36, pp. 1081-1089.
Bäumer, Kontakte, vol. 3, 1989, pp. 42-49.

* cited by examiner

Primary Examiner—Sanza L. McClendon
(74) Attorney, Agent, or Firm—Tyler A. Stevenson

(57) ABSTRACT

A process for the production of coatings with scratch-resistant durable surfaces that comprise as photoinitiator (B) in a photocurable formulation at least one surface-active photoinitiator, concentrated at the surface of the formulation, of formula (Ia) or (Ib), wherein $R_a$ is a radical of formula (IIa), $R_b$ is a radical of formula (IIb)), or $R_a$ and $R_b$ are naphthyl, anthracyl, phenanthryl or a heterocyclic radical each of which is unsubstituted or substituted; $R_1$, $R_2$, $R_3$, $R_4$, $R_5$, $R_6$, $R_7$, $R_8$, $R_9$ and $R_{10}$ are, for example, each independently of the others hydrogen; A-Y; $C_1$–$C_{12}$alkyl, halogen or phenyl; $R_{11}$ and $R_{12}$ are, for example, $C_1$–$C_{12}$ alkyl; X is —$OR_{20}$ or —$N(R_{21})(R_{22})$; $R_{20}$ is, for example, hydrogen or $C1$–$C4$alkyl; R21 and R22 are, for example, hydrogen or $C_1$–$C_{12}$ alkyl; $X_1$ is, for example, —O—; Y is, for example, a single bond or —O—; $Y_1$ is, for example, a single bond; and A is, for example, $C_6$–$C_{30}$alkyl.

5 Claims, No Drawings

SURFACE-ACTIVE PHOTOINITIATORS

The invention relates to a process for the production of scratch-resistant durable coatings in which surface-active photoinitiators are used, to novel surface-active photoinitiators, and to compositions comprising such photoinitiators.

Photoinitiators of the hydroxyalkylphenone type or aminoalkylphenone type are known in the art and some of those photoinitiators are available commercially. The synthesis of such photoinitiators is described, for example, in U.S. Pat. No. 4,315,807, U.S. Pat. No. 5,629,356, U.S. Pat. No. 5,795,985, U.S. Pat. No. 4,582,862, U.S. Pat. No. 4,960,746, U.S. Pat. No. 4,559,371, EP 287516, U.S. Pat. No. 5,532,112, WO 86/05777, WO 86/05778, DE 35 12 179, DE 41 04 183, DE 19 753 655, GB 2 320 027, EP 898 202, DE 19 907 957, EP 849 300 and JP 08 211 603.

In the coating industry, new, energy-saving curing mechanisms and applications causing as few emissions as possible are being sought for the production of durable scratch-resistant coatings. There is also a particular need to improve the surface of coatings, especially in respect of hardness, durability and gloss properties.

It has now been found that the desired properties can be attained by using certain photoinitiators in the coatings to be cured. For that purpose the photoinitiator is not distributed as homogeneously as possible in the formulation to be cured but concentrated specifically at the surface of the coating to be cured, specific orientation of the initiator towards the surface of the formulation thus taking place. To achieve this it is necessary to use photoinitiators having particular properties.

The invention relates to a process for the production of coatings having scratch-resistant durable surfaces, which comprises (1) preparing a photocurable formulation comprising
   (A) an ethylenically unsaturated polymerizable compound; and
   (B) a photoinitiator;
(2) applying the formulation to a substrate; and
(3) curing the formulation either
   solely by irradiation with electromagnetic radiation of a wavelength ranging from 200 nm into the IR region, or
   by irradiation with electromagnetic radiation of a wavelength ranging from 200 nm into the IR region and the prior, simultaneous and/or subsequent action of heat;

wherein the formulation comprises as photoinitiator (B) at least one surface-active photoinitiator, concentrated at the surface of the formulation, of formula Ia or Ib:

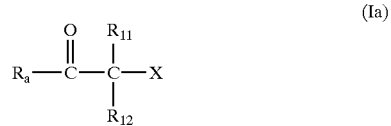
(Ia)

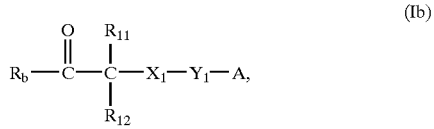
(Ib)

wherein
$R_a$ is a radical of formula IIa

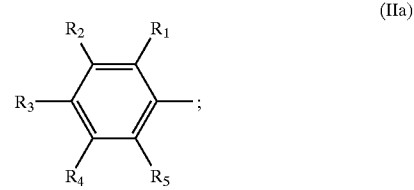
(IIa)

$R_b$ is a radical of formula IIb

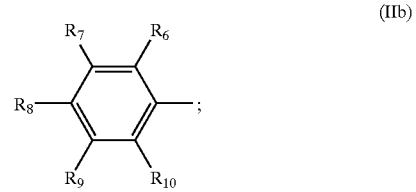
(IIb)

or
$R_a$ and $R_b$ are naphthyl, anthracyl, phenanthryl or a heterocyclic radical, the radicals naphthyl, anthracyl, phenanthryl and the heterocycle being unsubstituted or substituted by A-Y—, $C_1$–$C_8$alkyl, phenyl, $OR_{13}$, $SR_{14}$ or/and by $NR_{15}R_{16}$, and the substituents $OR_{13}$, $SR_{14}$ and $NR_{15}R_{16}$ being capable, by way of the radicals $R_{13}$, $R_{14}$, $R_{15}$ and/or $R_{16}$ together with further substituents on the naphthyl ring, anthracyl ring, phenanthryl ring or heterocycle or with one of the carbon atoms of the naphthyl ring, anthracyl ring, phenanthryl ring or heterocycle, of forming 5- or 6-membered rings; with the proviso that in the compounds of formula Ia at least one substituent A-Y— is present in the radical $R_a$;

$R_1$, $R_2$, $R_3$, $R_4$, $R_5$, $R_6$, $R_7$, $R_8$, $R_9$ and $R_{10}$ are each independently of the others hydrogen; A-Y—; $C_1$–$C_{12}$alkyl unsubstituted or substituted by OH, $C_1$–$C_4$alkoxy, phenyl, naphthyl, halogen, CN and/or by —O(CO)$R_{17}$; or $C_2$–$C_{12}$alkyl interrupted by one or more non-consecutive oxygen atoms; or $R_1$, $R_2$, $R_3$, $R_4$, $R_5$, $R_6$, $R_7$, $R_8$, $R_9$ and $R_{10}$ are $OR_{13}$, $SR_{14}$, $NR_{15}R_{16}$, halogen or unsubstituted or $C_1$–$C_4$alkyl- and/or $C_1$–$C_4$alkoxy-substituted phenyl, the substituents $OR_{13}$, $SR_{14}$, $NR_{15}R_{16}$ being capable, by way of the radicals $R_{13}$, $R_{14}$, $R_{15}$ and/or $R_{16}$ together with further substituents on the phenyl ring or with one of the carbon atoms of the phenyl ring, of forming 5- or 6-membered rings; with the proviso that in the compounds of formula IIa at least one radical $R_1$, $R_2$, $R_3$, $R_4$ or $R_5$ is A-Y—;

$R_{11}$ and $R_{12}$ are each independently of the other $C_1$–$C_{12}$alkyl, $C_2$–$C_8$alkenyl, $C_5$–$C_8$cycloalkyl or phenyl-$C_1$–$C_3$alkyl; or $R_{11}$ and $R_{12}$ together are $C_2$–$C_8$alkylene, $C_3$–$C_9$oxaalkylene or $C_3$–$C_9$azaalkylene;

$R_{13}$ and $R_{14}$ are each independently of the other hydrogen, $C_1$–$C_{12}$alkyl unsubstituted or substituted by OH, $C_1$–$C_4$alkoxy, phenyl, phenoxy or/and by —O(CO)$R_{17}$; or $C_2$–$C_{12}$-alkyl interrupted by one or more non-consecutive oxygen atoms; or $R_{13}$ and $R_{14}$ are phenyl, $C_3$–$C_6$alkenyl, cyclopentyl, cyclohexyl or naphthyl, those radicals being unsubstituted or substituted by $C_1$–$C_4$alkoxy, phenyl or/and by $C_1$–$C_4$alkyl;

$R_{15}$ and $R_{16}$ are each independently of the other hydrogen; $C_1$–$C_{12}$alkyl unsubstituted or substituted by OH, $C_1$–$C_4$alkoxy or/and by phenyl; or $C_2$–$C_{12}$alkyl interrupted by one or more non-consecutive oxygen atoms; or $R_{15}$ and $R_{16}$ are phenyl, —(CO)$R_{17}$ or —SO$_2R_{18}$; or $R_{15}$ and $R_{16}$, together with the nitrogen atom to which they are bonded, form a 5-, 6- or 7-membered ring that is optionally interrupted by —O— or by —N$R_{19}$—;

$R_{17}$ is $C_1$–$C_8$alkyl, or phenyl unsubstituted or substituted by $C_1$–$C_4$alkyl and/or by $C_1$–$C_4$alkoxy;

$R_{18}$ is $C_1$–$C_{12}$alkyl, unsubstituted phenyl, or phenyl substituted by $C_1$–$C_4$alkyl;

$R_{19}$ is hydrogen; $C_1$–$C_8$alkyl unsubstituted or substituted by OH or by $C_1$–$C_4$alkoxy; or phenyl unsubstituted or substituted by OH, $C_1$–$C_4$alkyl or by $C_1$–$C_4$alkoxy;

X is —O$R_{20}$ or —N($R_{21}$)($R_{22}$);

$R_{20}$ is hydrogen, $C_1$–$C_4$alkyl, $C_2$–$C_8$alkenyl or $C_1$–$C_4$alkanoyl;

$R_{21}$ and $R_{22}$ are each independently of the other hydrogen, $C_1$–$C_{12}$alkyl or $C_2$–$_6$alkenyl, or $R_{21}$ and $R_{22}$ together are $C_4$–$C_5$alkylene and, together with the nitrogen atom to which they are bonded, form a 5- or 6-membered ring that may be interrupted by —O— or by —N($R_{19}$)—; and $X_1$ is a radical —O—, —N($R_{19}$)— or —N(—$Y_1$-A)-;

Y is a single bond or —O—, —S—, —N($R_{19}$)—, —O—(CH$_2$)$_a$—, —O—(CH$_2$)$_a$—O—, —S—(CH$_2$)$_a$—, —O—(CH$_2$)$_a$—S—, —N($R_{19}$)—(CH$_2$)$_a$—, —O—(CH$_2$)$_a$—N($R_{19}$)—, —O—($C_2$–$C_{10}$alkenylene)-, —S—($C_2$–$C_{10}$alkenylene)-, —N($R_{19}$)—($C_2$–$C_{10}$alkenylene)-, —O—(CH$_2$)$_a$—O—($C_2$–$C_{10}$-alkenylene)-, —O—(CH$_2$)$_a$—S—($C_2$–$C_{10}$alkenylene)- or —O—(CH$_2$)$_a$N($R_{19}$)—($C_2$–$C_{10}$-alkenylene)-;

$Y_1$ is a single bond or —(CH$_2$)$_a$—O—, —(CH$_2$)$_a$—S—, —(CH$_2$)$_a$—N($R_{19}$)—, —($C_2$–$C_{10}$alkenylene)-O—, —($C_2$–$C_{10}$alkenylene)-S—, —($C_2$–$C_{10}$alkenylene)-N($R_{19}$)—, —($C_2$–$C_{10}$alkenylene)-O—(CH$_2$)$_a$—O—, —($C_2$–$C_{10}$alkenylene)-O—(CH$_2$)$_a$—S— or —($C_2$–$C_{10}$alkenylene)-O—(CH$_2$)$_a$—N($R_{19}$)—;

a is a number from 1 to 10;

A is $C_6$–$C_{30}$alkyl, $C_6$–$C_{30}$alkenyl, $C_6$–$C_{30}$alkynyl, $C_6$–$C_{30}$aralkyl, $C_6$–$C_{30}$alkyl-(CO)—, $C_6$–$C_{30}$alkenyl-(CO)—, $C_6$–$C_{30}$alkynyl-(CO)—, $C_6$–$C_{30}$aralkyl-(CO)—, $C_6$–$C_{30}$-alkyl-Si($R_{23}$)($R_{24}$)—, $C_6$–$C_{30}$alkenyl-Si($R_{23}$)($R_{24}$)— or $C_6$–$C_{30}$alkynyl-Si($R_{23}$)($R_{24}$)—, each of which radicals is unsubstituted or substituted by OH, $C_1$–$C_4$alkoxy, phenyl, naphthyl, halogen, CN, S$R_{14}$, N$R_{15}R_{16}$ and/or by —O(CO)$R_{17}$ and optionally interrupted by one or more —O—, —S— or —N$R_{19}$—; and $R_{23}$ and $R_{24}$ are each independently of the other $C_1$–$C_{19}$alkyl, phenyl, $C_2$–$C_6$hydroxyalkyl, $C_2$–$C_6$aminoalkyl or $C_5$–$C_8$cycloalkyl.

Some of the compounds of formula Ia and the compounds of the formula Ib are novel and the present Application relates likewise to those compounds of formulae Ia and Ib wherein $R_a$ and $R_b$ are each independently of the other a radical of formula IIa or IIb, $R_1$, $R_2$, $R_4$, $R_5$, $R_6$, $R_7$, $R_9$ and $R_{10}$ are hydrogen;

$R_3$ is A-Y'—;

$R_8$ is A-Y—;

$R_{11}$ and $R_{12}$ are each independently of the other $C_1$–$C_{12}$alkyl, especially methyl;

X is O$R_{20}$;

$R_{20}$ is hydrogen or $C_1$–$C_4$alkyl;

$X_1$ is a radical —O—;

Y is —O— or —O—(CH$_2$)$_a$—O—;

Y' is —O—(CH$_2$)$_a$—O—;

$Y_1$ is a single bond; and

A is $C_6$–$C_{30}$alkyl or $C_6$–$C_{30}$aralkyl.

$C_1$–$C_{12}$Alkyl is linear or branched and is, for example, $C_1$–$C_8$-, $C_1$–$C_6$- or $C_1$–$C_4$-alkyl. Examples include methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl and dodecyl.

$C_1$–$C_8$Alkyl and $C_1$–$C_4$alkyl have the same meanings as given above up to the corresponding number of carbon atoms.

$C_6$–$C_{30}$Alkyl is likewise linear or branched, for example: $C_6$–$C_{24}$-, $C_6$–$C_{12}$-, $C_{10}$–$C_{30}$-, $C_{10}$–$C_{24}$-, $C_{12}$–$C_{30}$-alkyl. Examples include hexyl, heptyl, 2,4,4-trimethylpentyl, 2-ethylhexyl, octyl, nonyl, decyl, undecyl, dodecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl and triacontyl.

$C_2$–$C_{12}$Alkyl interrupted by one or more oxygen atoms is interrupted, for example, from 1 to 9 times, e.g. from 1 to 7 times or once or twice, by —O—. When the radicals are interrupted by a plurality of oxygen atoms, the oxygen atoms are in each case separated from one another by at least one methylene group resulting, for example, in structural units such as —CH$_2$—O—CH$_3$, —CH$_2$CH$_2$—O—CH$_2$CH$_3$, —[CH$_2$CH$_2$O]$_y$—CH$_3$, in which y=from 1 to 9, —(CH$_2$CH$_2$O)$_7$CH$_2$CH$_3$, —CH$_2$—CH(CH$_3$)—O—CH$_2$—CH$_2$CH$_3$ or —CH$_2$—CH(CH$_3$)—O—CH$_2$CH$_3$.

$C_2$–$C_8$Alkylene is linear or branched, for example ethylene, propylene, isopropylene, n-butylene, sec-butylene, isobutylene, tert-butylene, pentylene, hexylene, heptylene or octylene. When $R_{11}$ and $R_{12}$ together are $C_2$–$C_8$alkylene they denote especially pentylene, that is to say, together with the carbon atom to which they are bonded they form a cyclohexyl ring, the following structures

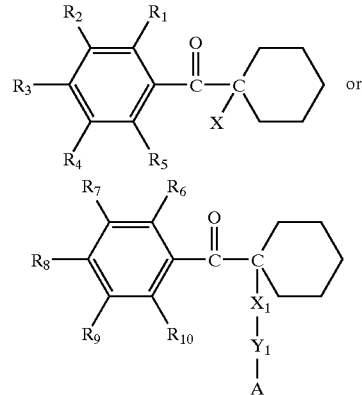

being understood.

$C_4$–$C_5$Alkylene has the same meanings as those given above, according to the number of carbon atoms.

As described above, $C_3$–$C_9$oxaalkylene is alkylene interrupted by —O— and $C_3$–$C_9$azaalkylene is alkylene interrupted by —N($R_{19}$)—.

$C_1$–$C_4$Alkanoyl is linear or branched and is, for example, formyl, acetyl, propionyl, butanoyl, or isobutanoyl.

$C_1$–$C_4$Alkoxy denotes linear or branched radicals and is, for example, methoxy, ethoxy, propoxy, isopropoxy, n-butyloxy, sec-butyloxy, isobutyloxy or tert-butyloxy, especially methoxy, ethoxy, propoxy, isopropoxy, n-butyloxy or tert-butyloxy, preferably methoxy.

$C_5$–$C_8$Cycloalkyl is linear or branched alkyl that contains at least one ring, for example cyclopentyl, methylcyclopentyl, cyclohexyl, methyl- or dimethyl-cyclohexyl, or cyclooctyl, especially cyclopentyl or cyclohexyl.

$C_2$–$C_8$Alkenyl may be mono- or poly-unsaturated and linear or branched and is, for example, $C_2$–$C_6$- or $C_2$–$C_4$-alkenyl. Examples include allyl, methallyl, 1,1-dimethylallyl, 1-butenyl, 2-butenyl, 1,3-pentadienyl, 1-hexenyl, heptenyl, 2,4,4-trimethyl-pentenyl, 2-ethylhexenyl and 1-octenyl, especially allyl. $R_{11}$ and $R_{12}$ denoting $C_2$–$C_8$alkenyl are, for example, $C_2$–$C_6$alkenyl, especially $C_2$–$C_4$alkenyl.

$C_3$–$C_6$Alkenyl may be mono- or poly-unsaturated and linear or branched and is, for example, $C_3$–$C_4$alkenyl. Examples include allyl, methallyl, 1,1-dimethylallyl, 1-butenyl, 2-butenyl, 1,3-pentadienyl and 1-hexenyl, especially allyl.

$C_6$–$C_{30}$Alkenyl is likewise linear or branched and mono- or poly-unsaturated and is, for example, $C_6$–$C_{24}$-, $C_6$–$C_{12}$-, $C_{10}$–$C_{30}$-, $C_{10}$–$C_{24}$- or $C_{12}$–$C_{30}$-alkenyl. Examples include hexenyl, heptenyl, 2,4,4-trimethyl-pentenyl, 2-ethylhexenyl, octenyl, nonenyl, decenyl, undecenyl, dodecenyl, tetradecenyl, pentadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl and triacontenyl.

$C_2$–$C_{10}$Alkenylene is a divalent radical that is mono- or poly-unsaturated and also linear or branched, for example $C_2$–$C_8$-, $C_2$–$C_6$-, $C_4$–$C_8$-, $C_3$–$C_6$-, or $C_2$–$C_4$-alkenylene. Examples include ethenylene, allylene, methallylene, 1,1-dimethylallylene, vinylene, 1-butenylene, 2-butenylene, 3-butenylene, 1,3-pentadlenylene, 1-hexenylene, 5-hexenylene, 1-octenylene and 7-octenylene, especially allylene.

$C_6$–$C_{30}$Alkynyl is linear or branched and mono- or poly-unsaturated and is, for example, $C_6$–$C_{24}$-, $C_6$–$C_{12}$-, $C_{10}$–$C_{30}$-, $C_{10}$–$C_{24}$- or $C_{12}$–$C_{30}$-alkynyl. Examples include hexynyl, heptynyl, 2,4,4-trimethylpentynyl, 2-thylhexynyl, octynyl, nonynyl, decynyl, undecynyl, dodecynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl and triacontynyl.

$C_6$–$C_{30}$Aralkyl is alkyl substituted by an aromatic radical. Examples include phenyl-$C_1$–$C_{24}$-alkyl, naphthyl-$C_1$–$C_{20}$alkyl, anthryl-$C_1$–$C_{16}$alkyl and phenanthryl-$C_1$–$C_{16}$alkyl, the alkyl radicals $C_1$–$C_{24}$-, $C_1$–$C_{20}$- and $C_1$–$C_{16}$- in question each being substituted by the corresponding aromatic radical phenyl, naphthyl, anthryl or phenanthryl respectively. The alkyl radicals are linear or branched and may have the meanings given above. Examples include benzyl, phenylethyl, α-methylbenzyl, phenylpentyl, phenylhexyl and α,α-dimethylbenzyl, especially benzyl, naphthylmethyl, naphthylethyl, naphthylpropyl and naphthyl-1-methylethyl, more especially naphthylmethyl. The alkyl unit may be in either the 1- or the 2-position of the naphthyl ring.

Halogen is fluorine, chlorine, bromine or iodine, especially chlorine or bromine, more especially fluorine.

Substituted phenyl is mono- to penta-substituted, for example mono-, di- or tri-substituted, especially mono- or di-substituted, on the phenyl ring.

A heterocyclic radical is to be understood in this context as meaning either an aliphatic or aromatic ring containing one or more, especially one or two, hetero atoms. It may also be a fused ring system. There come into consideration as hetero atoms, for example, especially O, N and S. Examples include furyl, thienyl, pyrrolyl, oxinyl, dioxinyl and pyridyl. 5- or 6-membered rings are preferred.

$R_a$ and $R_b$ denoting heterocyclic radicals are, for example, pyrrolyl, pyrrolidinyl, oxazolyl, pyridyl, 1,3-diazinyl, 1,2-diazinyl, piperidyl, morpholinyl, thianthrenyl, furanyl, pyranyl, xanthenyl, imidazolyl, thiazoylyl, pyrimidinyl, indazolinyl, indolyl, indazolyl, purinyl, isoquinolyl, quinolyl, xanthyl, thioxanthyl, acridinyl etc.

When $OR_{13}$-, $SR_{14}$- or $NR_{15}R_{16}$-substituted naphthyl, anthracyl, phenanthryl or heterocyclic rings, together with the radicals $R_{13}$, $R_{14}$, $R_{15}$ or/and $R_{16}$, form 5- or 6-membered rings, then, for example, the following structures are included

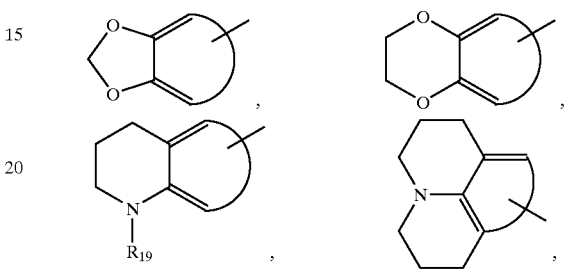

the arc and the two double bonds representing the aromatic ring in each case.

When $R_1$, $R_2$, $R_3$, $R_4$, $R_5$, $R_6$, $R_8$, $R_9$ or $R_{10}$ denoting $OR_{13}$, $SR_{14}$ or $NR_{15}R_{16}$, together with further substituents on the phenyl ring or with a carbon atom of the phenyl ring, form a 5- or 6-membered ring, then, for example, the following systems are included

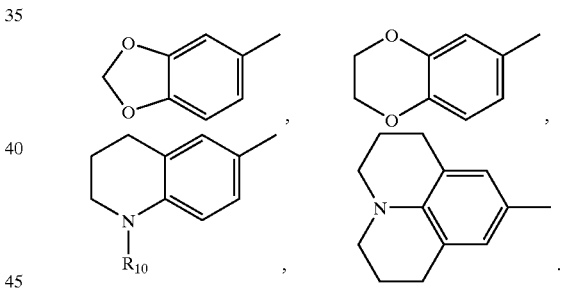

When $R_{15}$ and $R_{16}$, together with the nitrogen atom to which they are bonded, form a 5- or 6-membered ring that in addition may be interrupted by —O— or by —$NR_{19}$—, the ring is, for example, a saturated or unsaturated ring, for example aziridine, piperazine, pyrrole, pyrrolidine, oxazole, pyridine, 1,3-diazine, 1,2-diazine, piperidine or morpholine; morpholinyl, piperidyl or piperazinyl rings, especially, are formed.

$C_2$–$C_{10}$Alkenylene is mono- or poly-unsaturated, linear or branched, and is, for example, $C_2$–$C_8$-, $C_4$–$C_8$-, $C_3$–$C_6$- or $C_2$–$C_4$-alkenylene, e.g. ethenylene, 1-propenylene, 1-butenylene, 3-butenylene, 2-butenylene, 1,3-pentadienylene, 5-hexenylene or 7-octenylene.

$C_4$–$C_8$Alkenylene has the same meanings as those given above, according to the number of carbon atoms.

The expression "and/or" is intended to indicate that not only one of the defined alternatives (substituents) may be present, but equally a plurality of various of the defined alternatives (substituents) may be present simultaneously, that is to say mixtures of different alternatives (substituents).

The expression "at least" is intended to define one or more than one, for example one, two or three, preferably one or two.

The expression "ranging from 200 nm into the IR region" denotes from 200 nm to 2500 nm, especially from 200 nm to 800 nm or from 200 to 600 nm.

In the description and in the patent claims, unless expressly indicated otherwise the word "comprising" is to be understood as meaning that a defined entity or a defined group of entities are included, without, however, any other substances that have not been mentioned specifically being excluded.

"a" is preferably a number from 1 to 10, e.g. from 1 to 2, especially 2.

"A" is preferably a radical $C_6$–$C_{30}$alkyl.

Compounds of formula Ia are preferred.

In the compounds of formula Ia, at least one group —Y-A is present. When $R_a$ is a radical IIa, then, for example, from 1 to 3 or 1 or 2 or one of the substituents $R_1$, $R_2$, $R_3$, $R_4$ and $R_5$ is a group —Y-A. Preferably, 1 or 2 of the radicals $R_1$, $R_2$, $R_3$, $R_4$ and $R_5$ is/are —Y-A. More especially, $R_1$, $R_3$ or/and $R_5$ are a group —Y-A. Preferably, $R_3$ is a group —Y-A.

In the compounds of formula Ib, one of the substituents $R_6$, $R_7$, $R_8$, $R_9$ and $R_{10}$ is preferably a group —Y-A. For example, from 1 to 3 or 1 or 2 or one of the substituents $R_6$, $R_7$, $R_8$, $R_9$ and $R_{10}$ is a group —Y-A. Preferably, 1 or 2 of the radicals $R_6$, $R_7$, $R_a$, $R_9$ and $R_{10}$ is/are —Y-A. More especially, $R_6$, $R_8$ or/and $R_{10}$ are a group —Y-A. Preferably, $R_8$ is a group —Y-A.

Besides being a —Y-A group, $R_1$, $R_2$, $R_3$, $R_4$, $R_5$, $R_6$, $R_7$, $R_8$, $R_9$ and $R_{10}$ are especially hydrogen, $C_1$–$C_4$alkyl or $C_1$–$C_4$alkoxy, preferably hydrogen.

$R_{11}$ and $R_{12}$ are, for example, $C_1$–$C_4$alkyl, especially methyl. Preferably, $R_{11}$ and $R_{12}$ are methyl or together are $C_3$–$C_8$alkylene or, especially, together with the carbon atom to which they are bonded, form a cyclohexyl ring, or $R_{11}$ is $C_1$–$C_4$alkyl, especially ethyl, and $R_{12}$ is allyl or benzyl.

$R_{13}$ and $R_{14}$ are especially $C_1$–$C_4$alkyl, hydrogen, phenyl, or $C_2$–$C_8$alkyl interrupted by —O—, preferably $C_1$–$C_4$alkyl or hydrogen.

$R_{15}$ and $R_{16}$ are especially $C_1$–$C_4$alkyl, preferably methyl, or, together with the nitrogen atom to which they are bonded, form a morpholinyl radical.

$R_{17}$ is $C_1$–$C_8$alkyl, unsubstituted phenyl, or phenyl substituted by $C_1$–$C_4$alkyl and/or by $C_1$–$C_4$alkoxy;

$R_{18}$ is $C_1$–$C_{12}$alkyl, unsubstituted phenyl, or phenyl substituted by $C_1$–$C_4$alkyl;

$R_{19}$ is preferably hydrogen, $C_1$–$C_4$alkyl, or $C_1$–$C_4$alkyl substituted by OH.

X is preferably —$OR_{20}$ or $N(R_{21})(R_{22})$; $R_{20}$ is especially hydrogen, $R_{21}$ and $R_{22}$ are especially $C_1$–$C_4$alkyl, preferably methyl, or, together with the nitrogen atom to which they are bonded, form a morpholinyl radical.

$X_1$ is preferably —O—.

A is especially a $C_6$–$C_{30}$alkyl radical, which is unsubstituted or is substituted by halogen. Unsubstituted $C_6$–$C_{22}$alkyl is preferred.

Y is preferably a single bond, —O—, —S— or —O—$(CH_2)_a$—O—, especially —O— or —O—$(CH_2)_a$—O—, a being especially 2.

$Y_1$ is preferably a single bond or —$(CH_2)_a$—O—, especially a single bond.

The compounds of formula I are prepared according to customary methods known to the person skilled in the art.

I. Compounds of formulae Ia and Ib can be obtained, for example, by the customary reactions, known to the person skilled in the art, of ether formation or alkylation of a thiol group or of an amine group. For example, compounds of formulae Ia and Ib can be prepared by reacting a photoinitiator (III) with an alkyl halide (IV) in the presence of a base:

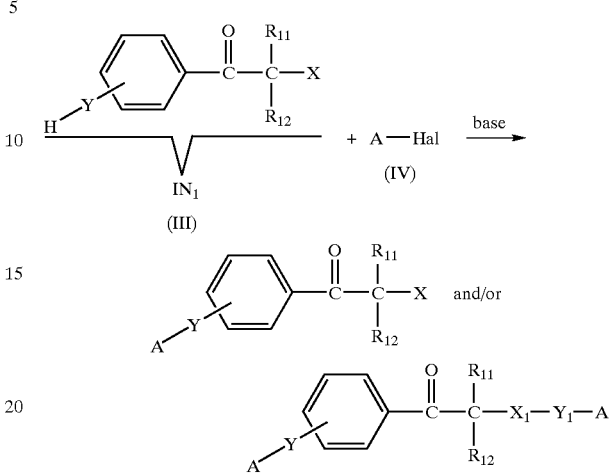

in which formulae $R_{11}$, $R_{12}$, Y, $Y_1$, X, $X_1$ and A are as defined hereinbefore. Such reactions are known to the person skilled in the art and are described in detail in the literature (e.g. J. March in Advanced Organic Chemistry, $3^{rd}$ edition 1985). When Y, for example, is —O—, the reaction corresponds to Williamson's ether formation (J. March in Advanced Organic Chemistry, $3^{rd}$ edition 1985, chapter 0–14, pages 342–343); when Y is —S—, the reaction is as described, e.g., in J. March in Advanced Organic Chemistry, $3^{rd}$ edition 1985, chapter 3–5, pages 589–590; when Y is —$NR_{19}$—, the reaction corresponds to the alkylation of an amine (J. March in Advanced Organic Chemistry, $3^{rd}$ edition 1985, chapter 0–45, pages 364–366).

II. Compounds of formula Ia can also be obtained by Friedel-Crafts alkylation of a photoinitiator (V) with an appropriate alkyl halide (IV) in the presence of a suitable catalyst:

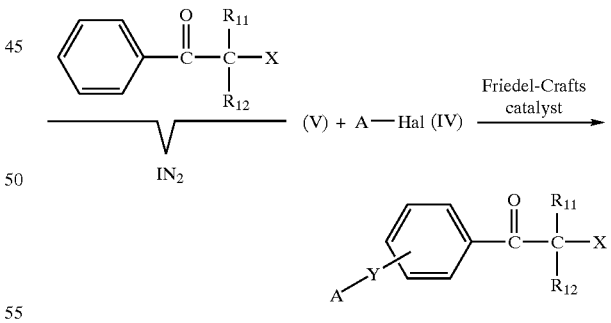

in which formulae $R_{11}$, $R_{12}$, Y and A are as defined hereinbefore; and X is $OR_{20}$ or $N(R_{21})(R_{22})$ wherein $R_{20}$, $R_{21}$ and $R_{22}$ are as defined hereinbefore, with the proviso that in this instance $R_{20}$, $R_{21}$ and $R_{22}$ are not hydrogen.

The procedure for such reactions is known to the person skilled in the art and is described in detail in the literature (e.g. J. March, Advanced Organic Chemistry, $3^{rd}$ edition 1985, chapter 1–13, pages 479–484; or Olah, "Friedel-Crafts Chemistry", Wiley NY 1973; and also Roberts and Khalaf, "Friedel-Crafts Alkylation Chemistry", Marcel Dekker NY 1984).

III. Compounds of formulae Ia and Ib can also be obtained by acylating corresponding photoinitiators in the presence of a base. The various possible conditions for such reactions are known to the person skilled in the art. For example, a compound Ia or Ib can be obtained by acylating a photoinitiator (III) with an appropriate surface-active reagent (VI) that contains an acid group or an acid chloride group to form an ester, a thiol ester or an amide:

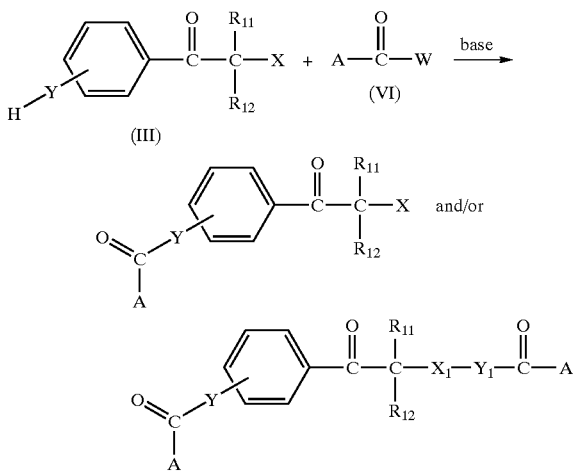

in which formulae $R_{11}$, $R_{12}$, X, $X_1$, Y, $Y_1$ and A are as defined hereinbefore; and W is OH or halogen, halogen being especially chlorine.

Such reactions are known to the person skilled in the art and are described in detail in customary organic chemistry textbooks, for example in J. March in Advanced Organic Chemistry, $3^{rd}$ edition 1985.

IV. Compounds of formula Ia can also be obtained by Friedel-Crafts acylation of a photoinitiator (V) with a surface-active reagent (VII) in the presence of a suitable catalyst. The various possible conditions for such reactions are known to the person skilled in the art. For example, a compound Ia can be obtained by acylation of a photoinitiator (V) with an appropriate surface-active reagent (VII) that contains an acid halide group:

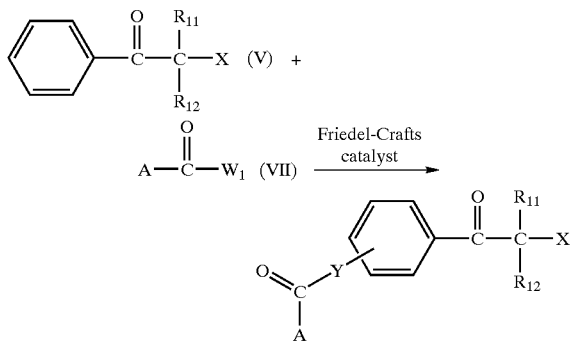

in which formulae $R_{11}$, $R_{12}$, Y and A are as defined hereinbefore; X is $OR_{20}$ or $N(R_{21})(R_{22})$ wherein $R_{20}$, $R_{21}$ and $R_{22}$ are as defined hereinbefore, with the proviso that in this instance $R_{20}$, $R_{21}$ and $R_{22}$ are not hydrogen; and $W_1$ is halogen, halogen being especially chlorine. The procedure for such reactions is known to the person skilled in the art and is described in detail in the literature (e.g. J. March, Advanced Organic Chemistry, $3^{rd}$ edition 1985, chapter 1–15, pages 484–487; or Olah, "Friedel-Crafts and Related Reactions", Interscience NY 1963–1964).

The reactions are carried out at various temperatures, depending on the solvents and starting materials employed. The temperatures and other reaction conditions required for the reactions in question are generally known and are familiar to the person skilled in the art. The reaction products can be separated and purified according to generally customary methods, for example by crystallisation, distillation or chromatography.

The photoinitiators (III) and (V) are in some cases available commercially, or they can be prepared according to methods known to the person skilled in the art, for example in accordance with the methods described in EP 3 002, EP 284 561, EP 805 152 and EP 281 941.

Preference is given to a process as described hereinbefore in which, in the compounds of formulae Ia and Ib, $R_a$ and $R_b$ are each independently of the other a radical of formula IIa or IIb or naphthyl that is unsubstituted or substituted by A-Y—, $C_1$–$C_8$alkyl or/and by $OR_{13}$;

$R_1$, $R_2$, $R_3$, $R_4$, $R_5$, $R_6$, $R_7$, $R_8$, $R_9$ and $R_{10}$ are each independently of the others hydrogen; A-Y—; $C_1$–$C_{12}$alkyl; or $C_2$–$C_{12}$alkyl interrupted by one or more non-consecutive oxygen atoms; or $R_1$, $R_2$, $R_3$, $R_4$, $R_5$, $R_6$, $R_7$, $R_8$, $R_9$ and $R_{10}$ are $OR_{13}$, halogen or phenyl;

$R_{11}$ and $R_{12}$ are each independently of the other $C_1$–$C_{12}$alkyl or phenyl-$C_1$–$C_3$alkyl; or $R_{11}$ and $R_{12}$ together are $C_2$–$C_8$alkylene;

$R_{13}$ is hydrogen; $C_1$–$C_{12}$alkyl; or $C_2$–$C_{12}$alkyl interrupted by one or more non-consecutive oxygen atoms;

X is $OR_{20}$ or $N(R_{21})(R_{22})$;

$R_{19}$ is hydrogen or $C_1$–$C_4$alkyl;

$R_{20}$ is hydrogen or $C_1$–$C_4$alkyl;

$R_{21}$ and $R_{22}$ are each independently of the other $C_1$–$C_{12}$alkyl or $C_2$–$C_6$alkenyl; or $R_{21}$ and $R_{22}$ together are $C_4$–$C_5$alkylene and, together with the nitrogen atom to which they are bonded, form a 5- or 6-membered ring that may be interrupted by O or by $N(R_{19})$;

$X_1$ is a radical —O—, —$N(R_{19})$— or —N(—$Y_1$-A)-;

Y is a single bond or —O—, —S— or —O—$(CH_2)_a$—O—;

$Y_1$ is a single bond; and

A is $C_6$–$C_{30}$alkyl or $C_6$–$C_{30}$aralkyl.

Special preference is given to a process in which, in the compounds of formulae Ia and Ib, $R_a$ and $R_b$ are each independently of the other a radical of formula IIa or IIb, $R_1$, $R_2$, $R_4$, $R_5$, $R_6$, $R_7$, $R_9$ and $R_{10}$ are hydrogen;

$R_3$ and $R_8$ are A-Y—;

$R_{11}$ and $R_{12}$ are each independently of the other $C_1$–$C_{12}$alkyl, especially methyl;

X is $OR_{20}$;

$R_{20}$ is hydrogen or $C_1$–$C_4$alkyl;

$X_1$ is a radical —O—;

Y is —O— or —O—$(CH_2)_a$—O—;

$Y_1$ is a single bond; and

A is $C_6$–$C_{30}$alkyl or $C_6$–$C_{30}$aralkyl.

The following are examples of compounds of formulae Ia and Ib according to the invention:

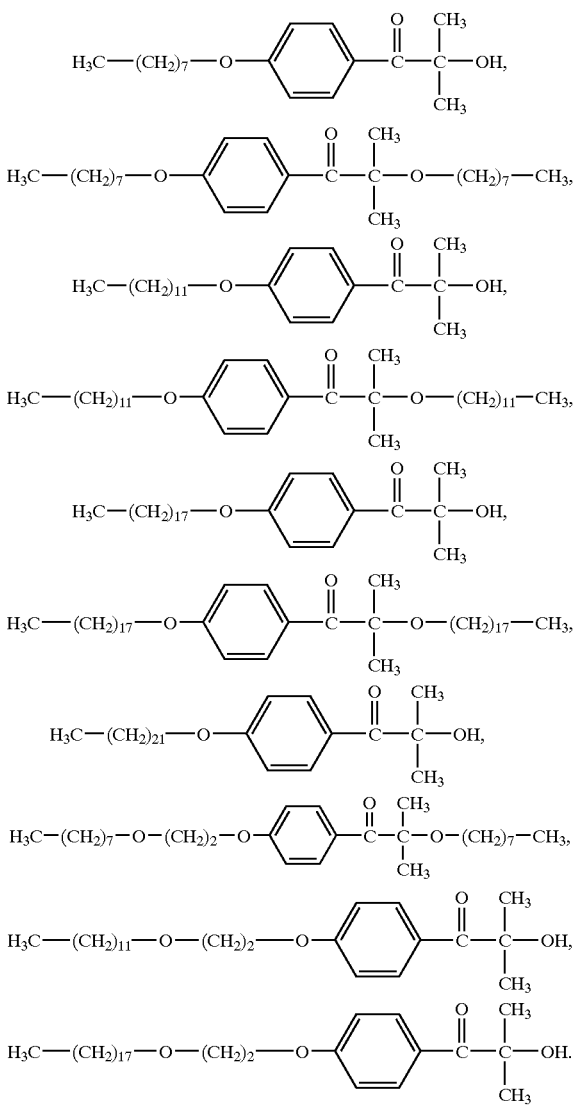

The compounds of formula I comprise at least one substituent —Y-A or —Y$_1$-A. Those substituents are the radicals that bring about the surface activity of the photoinitiator compounds, that is to say, ensure that the photoinitiator is concentrated at the surface of the formulation to be cured.

The photoinitiators are used in accordance with the invention to cure free-radical-polymerizable systems with the aim of obtaining a cured surface having excellent properties. It is crucial for that that the photoinitiator is concentrated at the surface of the formulation to be cured. As has already been stated above, this is achieved by appropriate substituents on the photoinitiator. An improvement in the surface properties can be achieved with the aid of such initiators not only in purely photocurable systems but also in formulations that are a mixture of thermally curable and photocurable. The present invention accordingly relates both to the use of the photoinitiators of formulae Ia and Ib in purely photocurable formulations and to the use of the photoinitiators of formulae Ia and Ib in formulations that are a mixture of photochemically and thermally curable. The thermal curing can be effected before, during or after the exposure to light.

The invention accordingly relates also to a process as described above in which the photocurable formulation comprises as further component at least one thermally crosslinkable compound (C), and the formulation is cured by irradiation with light of a wavelength ranging from 200 nm into the IR region, for example from 200 to 1000 nm, especially from 200 to 600 nm, and the prior, simultaneous and/or subsequent action of heat.

According to the invention, the compounds of formulae Ia and Ib can be used as surface-active photoinitiators for the photopolymerization of ethylenically unsaturated compounds or of mixtures that comprise such compounds, and are oriented towards the surface of the formulation in question.

According to the invention, a process for concentrating a photoinitiator at the surface of coatings comprises adding a surface-active photoinitiator of formula Ia or Ib to the photo-polymerizable mixture comprising the ethylenically unsaturated photopolymerizable compounds.

In compositions that comprise siloxane-modified resin components, it is not the concentration at the surface but rather the good miscibility that Is important.

It has been found that the initiators of formulae Ia and Ib are excellently suitable for increasing the miscibility and compatibility of the initiator molecule with such siloxane-modified resins.

The use as a surface-active photoinitiator is preferred.

The photoinitiators can also be used in combination with other photoinitiators (E) and/or further additives (D).

The invention accordingly relates also to photopolymerizable compositions comprising (A) at least one ethylenically unsaturated free-radical-photopolymerizable compound; and (B) at least one surface-active photoinitiator of formula Ia or Ib.

The invention relates furthermore to photopolymerizable compositions comprising (A) at least one ethylenically unsaturated free-radical-photopolymerizable compound, (B) at least one surface-active photoinitiator of formula Ia or Ib, and (C) at least one thermally crosslinkable compound.

In accordance with the invention, the compositions may also comprise further different photoinitiators (E) and/or further additives (D).

Catalysts for the thermal crosslinking may also be added. Suitable examples are listed hereinbelow.

The unsaturated compounds (A) may contain one or more olefinic double bonds. They may be low molecular weight (monomeric) or higher molecular weight (oligomeric). Colloidal dispersions of the oligomers in aqueous medium (latex) are also possible.

Examples of monomers having a double bond include alkyl and hydroxyalkyl acrylates and methacrylates, e.g. methyl, ethyl, butyl, 2-ethylhexyl and 2-hydroxyethyl acrylate, isobornyl acrylate and methyl and ethyl methacrylate. Also of interest are silicone acrylates. Further examples include acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having a plurality of double bonds are ethylene glycol diacrylate, propylene glycol diacrylate, neopentyl glycol diacrylate, hexamethylene glycol diacrylate and bisphenol-A diacrylate, 4,4'-bis(2-acryloyloxyethoxy)diphenylpropane, trimethylolpropane triacrylate, pentaerythritol triacrylate and pentaerythritol tetraacrylate, vinyl acrylate, divinyl-benzene, divinyl succinate, diallyl phthalate, triallyl phosphate, triallyl isocyanurate and tris(2-acryloylethyl) isocyanurate.

Examples of higher-molecular-weight (oligomeric) poly-unsaturated compounds are acrylated epoxy resins, acrylated or vinyl-ether- or epoxy-group-containing polyesters, polyurethanes and polyethers. Further examples of unsaturated oligomers include unsaturated polyester resins, which are usually prepared from maleic acid, phthalic acid and one or more diols and have molecular weights of about from 500 to 3000. In addition, it is also possible to use vinyl ether monomers and oligomers, and also maleate-terminated oligomers having polyester, polyurethane, polyether, polyvinyl ether and epoxide main chains. Combinations of vinyl-ether-group-carrying oligomers and polymers, as described in WO 90/01512, are especially suitable, but copolymers of monomers functionalized with vinyl ether and maleic acid also come into consideration.

Also suitable are compounds having one or more free-radical-polymerizable double bonds. Preferably, the free-radical-polymerizable double bonds in such compounds are in the form of (meth)acryloyl groups. (Meth)acryloyl and (meth)acryl, here and in the following, denote acryloyl and/or methacryloyl, and acryl and/or methacryl, respectively. Preferably at least two polymerizable double bonds in the form of (meth)acryloyl groups are present in the molecule. The compounds may be, for example, (meth)acryloyl-functional oligomeric and/or polymeric compounds of poly (meth)acrylate. The number average molar mass of such a compound may be, for example, from 300 to 10 000, preferably from 800 to 10 000. The compounds containing preferably free-radical-polymerizable double bonds in the form of (meth)acryloyl groups can be obtained according to customary methods, for example by reaction of poly(meth) acrylates with (meth)acrylic acid. That, and further methods of preparation, are described in the literature and are known to the person skilled in the art. Such unsaturated oligomers can also be termed prepolymers.

Functionalized acrylates are also suitable. Examples of suitable monomers normally used to form the backbone (the base polymer) of such functionalized acrylate and methacrylate polymers include, for example, acrylate, methylacrylate, methyl methacrylate, ethyl acrylate, ethyl methacrylate, n-butyl acrylate, n-butyl methacrylate, isobutyl acrylate, isobutyl methacrylate, 2-ethylhexyl acrylate, 2-ethylhexyl methacrylate etc. In addition, suitable amounts of functional monomers are copolymerized during the polymerization in order in that way to obtain the functional polymers. Acid-functionalized acrylate or methacrylate polymers are obtained using acid-functional monomers, such as acrylic acid and methacrylic acid. Hydroxyfunctional acrylate or methacrylate polymers are obtained from hydroxy-functional monomers, such as 2-hydroxyethyl methacrylate, 2-hydroxypropyl methacrylate, 3,4-dihydroxybutyl methacrylate. Epoxy-functionalized acrylate or methacrylate polymers are obtained using epoxy-functional monomers, such as glycidyl methacrylate, 2,3-epoxybutyl methacrylate, 3,4-epoxybutyl methacrylate, 2,3-epoxycyclohexyl methacrylate, 10,11-epoxyundecyl methacrylate etc. Similarly, it is possible, for example, for isocyanate-functionalized polymers to be prepared from isocyanate-functionalized monomers, for example meta-isopropenyl-α,α-dimethylbenzyl isocyanate.

There are especially suitable, for example, esters of ethylenically unsaturated mono- or poly-functional carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of suitable mono- or poly-functional unsaturated carboxylic acids are acrylic acid, methacrylic acid, crotonic acid, itaconic acid, cinnamic acid, maleic acid, fumaric acid, itaconic acid, and unsaturated fatty acids such as linolenic acid or oleic acid. Acrylic and methacrylic acid are preferred.

It is also possible, however, for saturated di- or poly-carboxylic acids to be used in admixture with unsaturated carboxylic acids. Examples of suitable saturated di- or poly-carboxylic acids include, for example, tetrachlorophthalic acid, tetrabromophthalic acid, phthalic acid anhydride, adipic acid, tetrahydrophthalic acid, isophthalic acid, terephthalic acid, trimellitic acid, heptanedicarboxylic acid, sebacic acid, dodecanedicarboxylic acid, hexahydrophthalic acid etc.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the said polyols, especially the aromatic polyols, and epichlorohydrin. Also suitable as polyols are polymers and copolymers that contain hydroxyl groups in the polymer chain or in side groups, e.g. polyvinyl alcohol and copolymers thereof and polymethacrylic acid hydroxyalkyl esters or co-polymers thereof. Further suitable polyols are oligo esters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified with one or with different unsaturated carboxylic acid(s), it being possible for the free hydroxyl groups in partial esters to be modified, for example etherified, or esterified with other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol tiacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diltaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligo ester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Also suitable as component (A) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di(β-aminoethoxy)- and di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Polybutadiene and polyisoprene and copolymers thereof are known. Suitable comonomers include, for example, olefins, such as ethylene, propene, butene and hexene, (meth)acrylates, acrylonitrile, styrene and vinyl chloride. Polymers having (meth)acrylate groups in the side chain are likewise known. Examples are reaction products of novolak-based epoxy resins with (meth)acrylic acid; homo- or co-polymers of vinyl alcohol or hydroxyalkyl derivatives thereof that have been esterified with (meth)acrylic acid; and homo- and co-polymers of (meth)acrylates that have been esterified with hydroxyalkyl (meth)acrylates.

The photopolymerizable compounds (A) can be used on their own or in any desired mixtures. Preferably, mixtures of polyol (meth)acrylates are used.

Binders may also be added to the compositions according to the invention, this being particularly advantageous when the photopolymerizable compounds are liquid or viscous substances. The amount of binder may be, for example, from 5 to 95% by weight, preferably from 10 to 90% by weight and especially from 40 to 90% by weight, based on total solids. The choice of the binder is made in accordance with the field of use and the properties required therefor, such as developability in aqueous and organic solvent systems, adhesion to substrates and sensitivity to oxygen.

Suitable binders are, for example, polymers having a molecular weight of approximately from 5000 to 2 000 000, preferably from 10 000 to 1 000 000. Examples are: homo- and co-polymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, such as cellulose acetate, cellulose acetate butyrate, methylcellulose, ethylcellulose; polyvinyl butyral, polyvinyl formal, cyclised caoutchouc, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly (ethylene/vinyl acetate), polymers such as polycaprolactam and poly(hexamethylene adipamide), polyesters such as poly(ethylene glycol terephthalate) and poly(hexamethylene glycol succinate).

There may also be used as component (A), that is to say as UV-curable component, the mentioned resins listed hereinbelow under (C1). Of special interest are, for example, unsaturated acrylates having reactive functional groups. The reactive functional group may be selected from a hydroxyl, thiol, isocyanate, epoxy, anhydride, carboxy, amino and a blocked amino group. Examples of OH-group-containing unsaturated acrylates are hydroxyethyl acrylates, hydroxybutyl acrylates and also glycidyl acrylates.

The unsaturated compounds can also be used in admixture with non-photopolymerizable film-forming components. These may be, for example, polymers that can be dried physically or solutions thereof in organic solvents, for example nitrocellulose or cellulose acetobutyrate, but they may also be chemically or thermally curable resins, for example polyisocyanates, polyepoxides or melamine resins. Melamine resins are to be understood as meaning not only condensation products of melamine (=1,3,5-triazine-2,4,6-triamine) but also condensation products of melamine derivatives. They are generally film-forming binders based on a thermoplastic or thermocurable resin, mainly on a thermocurable resin. Examples include alkyd resins, acrylic resins, polyester resins, phenol resins, melamine resins, epoxy resins and polyurethane resins and mixtures thereof. The concomitant use of thermally curable resins is important for use in so-called hybrid systems, which are both photopolymerized and thermally crosslinked.

Component (A) may be, for example, a coating composition comprising (A1) one or more compounds containing free-radical-polymerizable double bonds that, in addition, contain at least one further functional group that is reactive in terms of an addition and/or condensation reaction (examples are given hereinbefore), (A2) one or more compounds containing free-radical-polymerizable double bonds that, in addition, contain at least one further functional group that is reactive in terms of an addition and/or condensation reaction, the additional reactive functional group being complementary to, that is to say reactive with, the additional reactive functional group (s) of component (A1), (A3) optionally at least one monomeric, oligomeric and/or polymeric compound having at least one functional group that is reactive, in terms of an addition and/or condensation reaction, with respect to the functional groups of component (A1) or component (A2) present in addition to the free-radical-polymerizable double bonds.

Component (A2) carries the relevant groups complementary to, that is to say reactive with, component (A1). It is also possible for different kinds of functional group to be present in one component. With component (A3), there is a further component available that contains functional groups reactive in terms of addition and/or condensation reactions, those groups being able to react with the functional groups of (A1) or (A2) present in addition to the free-radicalpolymerizable double bonds. Component (A3) does not contain any free-radical-polymerizable double bonds. Examples of such (A1), (A2), (A3) combinations are to be found in WO 99/55785. Examples of suitable reactive functional groups are selected, for example, from hydroxyl, isocyanate, epoxy, anhydride, carboxyl and blocked amino groups. Examples are described hereinbefore.

Constituents of component (C) include, for example, thermally curable surface-coating or coating-system constituents customary in the art. Where appropriate, component (C) accordingly consists of a plurality of constituents.

Examples of component (C) include, for example, oligomers and/or polymers derived from $\alpha,\beta$-unsaturated acids and derivatives thereof, e.g. polyacrylates and polymethacrylates, polymethyl methacrylates modified in respect of impact resistance using butyl acrylate, polyacrylamides and polyacrylonitriles. Further examples of component (C) are urethanes, polyurethanes that are derived on the one hand from polyethers, polyesters and polyacrylates having free hydroxyl groups or thiol groups and on the other hand from aliphatic or aromatic polyisocyanates, and precursors thereof. Accordingly component (C) includes, for example, also crosslinkable acrylic resins derived from substituted acrylic acid esters, e.g. epoxy acrylates, urethane acrylates or polyester acrylates. In addition, alkyd resins, polyester resins and acrylate resins and modifications thereof that are crosslinked with melamine resins, urea resins, isocyanates, isocyanurates, polyisocyanates, polyisocyanurates and epoxy resins, can be constituents of component (C).

Component (C) is, for example, generally a film-forming binder based on a thermoplastic or thermocurable resin, chiefly on a thermocurable resin. Examples include alkyd resins, acrylic resins, polyester resins, phenol resins, melamine resins, epoxy resins, polyurethane resins and mixtures thereof. Examples of such resins are described, for example, in Ullmann's Encyclopedia of Industrial Chemistry, 5th Edition, Vol. A18, pp. 368–426, VCH, Weinheim 1991.

Component (C) can be a cold-curable or a hot-curable binder, the addition of a curing catalyst possibly being advantageous. Suitable catalysts for accelerating the full cure of the binder are described, for example, in Ullmann's Encyclopedia of Industrial Chemistry, Vol. A18, p. 469, VCH Verlagsgesellschaft, Weinheim 1991.

The following are examples of special binders suitable as component (C):

1. surface-coating compositions based on cold- or hot-crosslinkable alkyd, acrylate, polyester, epoxy or melamine resins or mixtures of such resins, optionally with the addition of a curing catalyst;
2. two-component polyurethane surface-coating compositions based on hydroxyl-group-containing acrylate, polyester or polyether resins and aliphatic or aromatic isocyanates, isocyanurates or polyisocyanates;
3. two-component polyurethane coating compositions based on thiol-group-containing acrylate, polyester or polyether resins and aliphatic or aromatic isocyanates, isocyanurates or polyisocyanates;
4. one-component polyurethane surface-coating compositions based on blocked isocyanates, isocyanurates or polyisocyanates which are deblocked during stoving; the addition of melamines is also possible, if desired;
5. one-component polyurethane surface-coating compositions based on aliphatic or aromatic urethanes or polyurethanes and hydroxyl-group-containing acrylate, polyester or polyether resins;
6. one-component polyurethane surface-coating compositions based on aliphatic or aromatic urethane acrylates or polyurethane acrylates having free amine groups in the urethane structure and melamine resins or polyether resins, optionally with the addition of a curing catalyst;
7. two-component surface-coating compositions based on (poly)ketimines and aliphatic or aromatic isocyanates, isocyanurates or polyisocyanates;
8. two-component surface-coating compositions based on (poly)ketimines and an unsaturated acrylate resin or a polyacetoacetate resin or a methacrylamidoglycolate methyl ester;
9. two-component surface-coating compositions based on carboxyl- or amino-group-containing polyacrylates and polyepoxides;
10. two-component surface-coating compositions based on anhydride-group-containing acrylate resins and a polyhydroxy or polyamino component;
11. two-component surface-coating compositions based on acrylate-containing anhydrides and polyepoxides;
12. two-component surface-coating compositions based on (poly)oxazolines and anhydride-group-containing acrylate resins or unsaturated acrylate resins or aliphatic or aromatic isocyanates, isocyanurates or polyisocyanates;
13. two-component surface-coating compositions based on unsaturated (poly)acrylates and (poly)malonates;
14. thermoplastic polyacrylate surface-coating compositions based on thermoplastic acrylate resins or extrinsically crosslinking acrylate resins in combination with etherified melamine resins;
15. surface-coating systems, especially clear lacquers, based on malonate-blocked isocyanates with melamine resins (e.g. hexamethoxymethylmelamine) as crosslinkers (acid-catalysed);
16. UV-curable systems based on oligomeric urethane acrylates and/or acylate acrylates, optionally with the addition of other oligomers or monomers;
17. dual-cure systems, which are cured first thermally and then by UV, or vice versa, the constituents of the surface-coating formulation comprising double bonds that can be caused to react by UV light and photoinitiators and/or by electron beam curing.

Blocked isocyanates as may be employed, inter alia, in component (C) are described, for example, in Organischer Metallschutz: Entwicklung und Anwendung von Beschichtungs-stoffen [Organic Protection of Metals: Development and Application of Coating Materials], page 159–160, Vincentz Verlag, Hannover (1993). These are compounds in which the highly reactive NCO group is "blocked" by reaction with specific radicals, such as primary alcohols, phenol, acetoacetates, $\epsilon$-caprolactam, phthalimide, imidazole, oxime or amine. The blocked isocyanate is stable in liquid systems and also in the presence of hydroxyl groups. On heating, the blocking agents are eliminated and the NCO group is exposed.

Both 1-component (1K) and 2-component (2K) systems may be used as component (C). Examples of such systems are described in Ullmann's Encyclopedia of Industrial Chemistry, Vol. A18, Paints and Coatings, page 404–407, VCH Verlagsgesellschaft mbH, Weinheim (1991).

The composition may be optimised by specially adapting the formulation, for example by varying the binder/crosslinker ratio. Such measures are well known to the person skilled in the art of coatings technology.

In the curing process of the invention the component (C) is preferably a mixture based on acrylate/melamine (and melamine derivatives), 2-component polyurethane, 1-component polyurethane, 2-component epoxy/carboxy or 1-component epoxy/carboxy. Mixtures of these systems are also possible, an example being the addition of melamine (or derivatives thereof) to 1-component polyurethanes.

Component (C) Is preferably a binder based on a polyacrylate with melamine or on a melamine derivative. Preference is also given to a system based on a polyacrylate polyol and/or polyester polyol with an unblocked polyisocyanate or polyisocyanurate.

Component (C) may further comprise monomeric and/or oligomeric compounds containing ethylenically unsaturated bonds (prepolymers) which additionally contain at least one or more OH, $NH_2$, COOH, epoxy or NCO groups (=C1) capable of reaction with the binder and/or crosslinker substituent of component (C). Following application and thermal curing, the ethylenically unsaturated bonds are converted by UV radiation into a crosslinked, high molecular mass form. Examples of such components (C) are described, for example, in the above-mentioned publication Ullmann's Encyclopedia of Industrial Chemistry, 5th Ed., Vol. A18, pages 451–453, or by S. Urano, K. Aoki, N. Tsuboniva and R. Mizuguchi in Progress in Organic Coatings, 20 (1992), 471–486, or by H. Terashima and O. Isozaki in JOCCA 1992 (6), 222.

(C1) may be, for example, an OH-containing unsaturated acrylate, e.g. hydroxyethyl or hydroxybutyl acrylate or else glycidyl acrylates. The component (C1) may be of any desired construction (e.g. polyester, polyacrylate, polyether, etc., units) provided there are an ethylenically unsaturated double bond and also free OH, COOH, $NH_2$, epoxy or NCO groups. (C1) may also be obtained, for example, by reacting an epoxy-functional oligomer with acrylic acid or methacrylic acid. A typical example of an OH-functional oligomer containing vinylic double bonds is

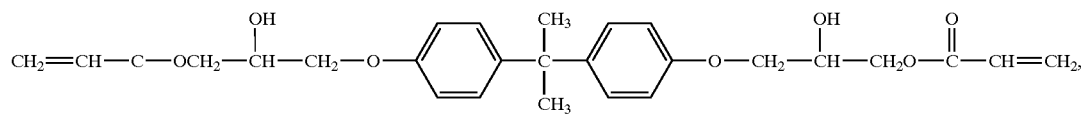

obtained by reacting $CH_2$=CHCOOH with

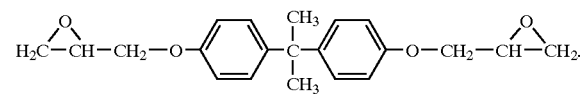

One possibility for preparing component (C1) is also, for example, the reaction of an oligomer that contains only one epoxy group and at another site in the molecule possesses a free OH group.

The ratio of components (A) to (C) in the UV-crosslinking and thermally crosslinking formulations is not critical. "Dual-cure" systems are well known to the person skilled in the art, who is therefore well aware of the optimum proportions of the UV-crosslinkable and thermally crosslinkable components for the particular desired application. For example, the compositions may comprise components (A) and (C) in a ratio of from 5:95 to 95:5, from 20:80 to 80:20 or from 30:70 to 70:30, e.g. from 40:60 to 60:40.

Examples of "dual-cure" systems, i.e. systems containing both UV-curable and thermally curable components, may be found, inter alia, in U.S. Pat. No. 5,922,473, columns 6 to 10.

To the compositions that are used in the process of the invention it is also possible to add solvents or water. Where the compositions are used without solvents, they comprise, for example, powder coating formulations. Suitable solvents are solvents which are known to the person skilled in the art and are customary particularly in coatings technology. Examples are various organic solvents, such as ketones, e.g. methyl ethyl ketone, cyclohexanone; aromatic hydrocarbons, e.g. toluene, xylene or tetramethylbenzene; glycol ethers, such as diethylene glycol monoethyl ether, dipropylene glycol diethyl ether; esters, such as ethyl acetate; aliphatic hydrocarbons, such as hexane, octane, decane; or petroleum solvents, such as petroleum ether.

The invention also provides compositions comprising as component (A) at least one ethylenically unsaturated photopolymerizable compound in emulsion or solution in water. Such radiation-curable aqueous prepolymer dispersions are available commercially in numerous variations. They are understood to comprise a dispersion of water and at least one prepolymer dispersed therein. The concentration of the water In these systems is, for example, from 5 to 80, in particular from 30 to 60% by weight. The radiation-curable prepolymer or prepolymer mixture is present, for example, in concentrations of from 95 to 20, in particular from 70 to 40% by weight. In these compositions the sum of the percentages stated for water and prepolymers is in each case 100; the auxiliaries and additives are extra in different amounts depending on the intended use.

The radiation-curable film-forming prepolymers which are in dispersion and often also in solution in water comprise monofunctional or polyfunctional ethylenically unsaturated prepolymers which are known per se for aqueous prepolymer dispersions, may be initiated by means of free radicals, and have a polymerizable double bond content of, for example, from 0.01 to 1.0 mol per 100 g of prepolymer and also have an average molecular weight of, for example, at least 400, in particular from 500 to 10 000. Depending on the intended application, however, prepolymers with higher molecular weights may also be suitable.

Use is made, for example, of polyesters containing polymerizable C—C double bonds and having an acid number of not more than 10, polyethers containing polymerizable C—C double bonds, hydroxyl-containing reaction products of a polyepoxide containing at least two epoxide groups per molecule with at least one α,β-ethylenically unsaturated carboxylic acid, polyurethane (meth)acrylates, and also acrylic copolymers containing α,β-ethylenically unsaturated acrylic radicals, as described, for example, in EP 012339. Mixtures of these prepolymers may likewise be used. Examples of further suitable prepolymers include the polymerizable prepolymers described in EP 033896, which are thioether adducts of polymerizable prepolymers having an average molecular weight of at least 600, a carboxyl group content of from 0.2 to 15% and a polymerizable C—C double bond content of from 0.01 to 0.8 mol per 100 g of prepolymer. Other suitable aqueous dispersions based on specific alkyl (meth)acrylate polymers are described in EP 041125; suitable water-dispersible, radiation-curable prepolymers comprising urethane acrylates are given, for example, in DE 2936039.

As further additions, these radiation-curable aqueous prepolymer dispersions may comprise dispersing aids, emulsifiers, antioxidants, light stabilizers, dyes, pigments, fillers, e.g. talc, gypsum, silica, rutile, carbon black, zinc oxide, iron oxides, reaction accelerants, levelling agents, lubricants, wetting agents, thickeners, matting agents, defoamers, and other auxiliaries customary in coatings technology. Suitable dispersing aids include water-soluble organic compounds of high molecular mass containing polar groups, such as polyvinyl alcohols, polyvinylpyrrolidone or cellulose ethers. Emulsifiers which can be used include nonionic, and possibly also ionic, emulsifiers.

The compounds of the invention and mixtures thereof may also be used as free-radical photoinitiators or photoinitiating systems for radiation-curable powder coating materials. The powder coating materials may be based on solid resins and monomers containing reactive double bonds, such as maleates, vinyl ethers, acrylates, acrylamides and mixtures thereof. A free-radically UV-curable powder coating material may be formulated by mixing unsaturated polyester resins with solid acrylamides (e.g. methylacrylamidoglycolate methyl ester) and a free-radical photoinitiator of the invention, as described for example in the paper "Radiation Curing of Powder Coating", Conference Proceedings, Radtech Europe 1993 by M. Wittig and Th. Gohmann. Free-radically UV-curable powder coating materials may also be formulated by mixing unsaturated polyester resins with solid acrylates, methacrylates or vinyl ethers and a photoinitiator (or photoinitiator mixture) of the invention. The powder coating materials may also include binders, as described for example In DE 4228514 and EP 636669. The powder coating formulations described in EP 636669 contain, for example, a) an unsaturated resin from the group of the (semi)crystalline or amorphous unsaturated polyesters, unsaturated polyacrylates or mixtures thereof with unsaturated polyesters, particular preference being given to those derived from maleic acid or fumaric acid; b) an oligomeric or polymeric crosslinking agent containing vinyl ether-functional, vinyl ester-functional or (meth)acrylate-functional groups, particular preference being given to vinyl ether oligomers, such as divinyl ether-functionalized urethanes; c) the photoinitiator. The UV-curable powder coating materials may also comprise white or coloured pigments. For example, preferably rutile titanium dioxide may be used in concentrations of up to 50% by weight in order to give a cured powder coating possessing good hiding power. The technique normally involves applying the powder to the substrate, such as metal or wood, by electrostatic or tribostatic spraying, melting the powder by heating and, after a smooth film has formed, radiation-curing the coating with ultraviolet and/or visible light, using medium-pressure mercury lamps, metal halide lamps or xenon lamps, for example. A particular advantage of the radiation-curable powder coating materials over their thermally curable counterparts is that the flow time after melting of the powder particles may be selectively extended in order to ensure the formation of a smooth, highly glossy coating. Unlike thermally curable systems, radiation-curable powder coating materials may be formulated without the unwanted effect of a shortened lifetime in such a way that they melt at relatively low temperatures. For this reason they are also suitable as coatings for heat-sensitive substrates, such as wood or plastics.

Where the powder coating materials are not to be applied to heat-sensitive substrates, as in the case of metals (vehicle coatings), however, it is also possible to provide dual-cure powder coating formulations with the photoinitiators of the invention. The person skilled in the art knows such formulations; they are cured both thermally and by means of UV. Formulations of this kind are given, for example, in U.S. Pat. No. 5,922,473.

Besides the photoinitiators of the invention, the powder coating formulations may also comprise UV absorbers. Appropriate examples are listed later on below.

The photopolymerizable mixtures can also contain various additives (D) in addition to the photoinitiator. Examples thereof are thermal inhibitors, which are intended to prevent premature polymerization, e.g. 2,2,6,6-tetramethyl-4-hydroxypiperidin-1-oxyl (4-hydroxy-TEMPO) and derivatives thereof, e.g. bis(2,2,6,6-tetramethylpiperidin-1-oxyl-4-yl)-decanedioate or polyalkyl-piperidine-N-oxyl free radicals, 3-arylbenzofuran-2-one and derivatives thereof, e.g. 5,7-di-tert-butyl-3-phenyl-3H-benzofuran-2-one (as described, for example, in WO 01/42313), hydroquinone, hydroquinone derivatives, p-methoxyphenol, β-naphthol and sterically hindered phenols, e.g. 2,6-di(tert-butyl)-p-cresol. In order to increase dark-storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerization it is possible to add paraffin or similar wax-like substances which, being insoluble in the polymer, migrate to the surface at the beginning of the polymerization and form a transparent surface layer which prevents air from entering. Equally possible is the application of a layer that is impermeable to oxygen. As light stabilizers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

The following are examples of such UV absorbers and light stabilizers:

1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2- octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH₂CH₂—COO—CH₂CH₂]₂— where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl] benzotriazole.

2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3. Esters of substituted and unsubstituted benzoic acids, as for example 4-tert-butyl-phenyl salicylate, phenyl salicylate, octylphenyl salicylate, dibenzoyl resorcinol, bis(4-tert-butyl-benzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

5. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperdyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butyl-amino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane and epichlorohydrin, 1,1-bis-(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

8. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-iso-octyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo [triethyltris(3,3',5,5'-tetra-tert-butyl-1,1'-biphenyl-2,2'-diyl)phosphite], 2-ethyl-hexyl(3,3',5,5'-tetra-tert-butyl-1,1'-biphenyl-2,2'-diyl)phosphite, 5-butyl-5-ethyl-2-(2,4,6-tert-butylphenoxy)-1,3,2-dioxaphosphirane.

Furthermore, it is possible to use additives customary in the art, such as antistatics, flow improvers and adhesion promoters.

Owing to the surface activity of the compounds of the invention it is also possible to use these compounds as flow improvers, either alone or in combination with further customary flow improvers.

The invention further provides for the use of compounds of the formulae Ia and Ib as flow improvers, alone or in combination with further, customary flow improvers.

DIN 55945 defines levelling as "the more or less pronounced capacity of a still-liquid coating itself to compensate the unevennesses which arise in the course of its application." (cf. J. Bieleman, Lackadditive [Additives for Coatings], VCH Weinheim 1998, chapter 6). The levelling of a coating material depends greatly on its flow behaviour and on its surface tension. Flow improvers are substances which help wet coatings to become films which flow out evenly, by reducing the viscosity and/or surface tension. In the case of powder coating materials, flow improvers also lower the melt viscosity and the glass transition temperature and have an additional devolatilizing effect. Flow improvers are used to eliminate levelling defects or surface defects which detract from the overall appearance of the coating. Levelling defects or surface defects include the orange peel effect, formation of structures, cratering, fisheyes, sensitivity to draughts, substrate wetting problems, brush marks, runs, bittiness, pinholes, etc. The use of the compounds of the invention as flow improvers makes it possible to lower the surface tension. The surface tension may be calculated by determining the marginal angle of a drop of liquid on a surface (contact angle measurement).

In order to accelerate the photopolymerization, there may be added as further additives (D) amines, especially tertiary amines, for example tributylamine, triethanolamine, p-dimethylaminobenzoic acid ethyl ester, Michler's ketone, N-methyl-diethanolamine, N-dimethylethanolamine, N-ethylmorpholine, N-methylmorpholine, diazabicyclooctane (triethylenediamine), 18-diazabicyclo[5.4.0]undec-7-ene (DBU), 1,5-diazabicyclo[4.3.0]non-5-ene (DBN) and salts thereof. Further examples include quaternary ammonium salts, for example trimethylbenzylammonium chloride. The action of the amines can be enhanced by the addition of aromatic ketones of the benzophenone type. Amines suitable for use as oxygen capture agents are, for example, substituted N,N-dialkylanilines, as described in EP 339 841. Further accelerators, co-initiators and auto-oxidisers are thiols, thioethers, disulfides and phosphines, as described e.g. in EP 438 123 and GB 2 180 358.

It is also possible to add chain transfer reagents customary in the art to the compositions of the invention. Examples are mercaptans, amines and benzothiazole.

The photopolymerization may further be accelerated by adding photosensitizers as further additives (D), which shift or broaden the spectral sensitivity. These photosensitizers are, in particular, aromatic carbonyl compounds such as benzophenone derivatives, thioxanthone derivatives, and also especially isopropylthioxanthone, anthraquinone derivatives and 3-acylcoumarin derivatives, terphenyls, styryl ketones, and also 3-(aroylmethylene)thiazolines, camphorquinone, and also eosine dyes, rhodamine dyes and erythrosine dyes.

The amines indicated above, for example, may also be regarded as photosensitizers.

The curing process, especially of compositions which are pigmented (with titanium dioxide for example), may also be assisted by adding an additional additive (D) which is a component which under thermal conditions forms free radicals, such as an azo compound, for instance 2,2'-azobis(4-methoxy-2,4-dimethylvaleronitrile), a triazene, diazo sulfide, pentazadiene or a peroxy compound such as hydroperoxide or peroxycarbonate, e.g. t-butyl hydroperoxide, as described for example in EP 245639.

As further additives (D), the compositions may also comprise, for example, a photoreducible dye, such as xanthene, benzoxanthene, benzothioxanthene, thiazine, pyronine, porphyrin or acridine dyes, and/or a radiation-cleavable trihalomethyl compound. Similar compositions are described, for example, in EP 445624

Further common additives (D)—depending on the intended use—include optical brighteners, fillers, e.g. kaolin, talc, barytes, gypsum, chalk or silicatic fillers, pigments, dyes, wetting agents or flow improvers.

For the curing of thick and pigmented coatings it is appropriate to add glass microbeads or pulverized glass fibres, as described for example in U.S. Pat. No. 5,013,768.

The formulations may also comprise dyes and/or white or coloured pigments. Depending on the intended application, both organic and inorganic pigments may be used. Such additions are known to the person skilled in the art; some examples are titanium dioxide pigments, of, for example, the ruble or anatase type, carbon black, zinc oxide, such as zinc white, iron oxides, such as yellow iron oxide, red iron oxide, chrome yellow, chrome green, nickel titanium yellow, ultramarine blue, cobalt blue, bismuth vanadate, cadmium yellow or cadmium red. Examples of organic pigments are monoazo or disazo pigments, and also metal complexes thereof, phthalocyanine pigments, polycyclic pigments, such as perylene, anthraquinone, thioindigo, quinacridone or triphenylmethane pigments, and also diketopyrrolopyrrole, isoindolinone, e.g. tetrachloroisoindolinone, isoindoline, dioxazine, benzimidazolone and quinophthalone pigments.

The pigments may be used individually or else in a mixture in the formulations.

The pigments, depending on the intended use, are added to the formulations in the amounts customary in the art, for example in an amount of from 1 to 60% by weight, or from 10 to 30% by weight, based on the overall mass.

The formulations may also, for example, comprise organic dyes from a very wide variety of classes. Examples are azo dyes, methine dyes, anthraquinone dyes or metal complex dyes. Customary concentrations are, for example, from 0.1 to 20%, in particular from 1 to 5%, based on the overall mass.

The choice of additives is guided by the respective field of application and by the properties desired for this field. The above-described additives (D) are customary in the art and, accordingly, are used in the amounts that are customary in the art.

In certain cases it may be of advantage to use mixtures of two or more of the photoinitiators of the formula Ia and/or Ib; it is advantageous, for example, to use mixtures obtained directly in the preparation. It is of course also possible to use mixtures with known photoinitiators (E), examples being mixtures with camphorquinone, benzophenone, benzophenone derivatives, acetophenone, acetophenone derivatives, such as α-hydroxycycloalkyl phenyl ketones or 2-hydroxy-2-methyl-1-phenylpropanone, dialkoxyacetophenones, α-hydroxy- or α-aminoacetophenones, such as (4-methylthiobenzoyl)-1-methyl-1-morpholinoethane, (4-morpholinobenzoyl)-1-benzyl-1-dimethylaminopropane, 4-aroyl-1,3-dioxolanes, benzoin alkyl ethers and benzil ketals, such as benzil dimethyl ketal, phenylglyoxalates and derivatives thereof, dimeric phenylglyoxalates, peresters, for example benzophenonetetracarboxylic peresters as described for example in EP 126541, monoacylphosphine oxides, such as (2,4,6-trimethylbenzoyl)phenylphosphine oxide, bisacylphosphine oxides, such as bis(2,6-dimethoxybenzoyl)(2,4,4-trimethylpent-1-yl)phosphine oxide, bis(2,4,6-trimethyl-benzoyl)phenylphosphine oxide or bis(2,4,6-trimethylbenzoyl)(2,4-dipentoxyphenyl)phosphine oxide, trisacylphosphine oxides, halomethyltriazines, e.g. 2-[2-(4-methoxyphenyl)-vinyl]-4,6-bistrichloromethyl[1,3,5]triazine, 2-(3,4-methoxyphenyl)-4,6-bistrichloromethyl-[1,3,5] triazine, 2-(3,4-dimethoxyphenyl)-4,6-bistrichloromethyl[1,3,5]triazine, 2-methyl-4,6-bistrichloromethyl[1,3,5]triazine, hexaarylbisimidazole/coinitiator systems, e.g. ortho-chlorohexaphenylbisimidazole together with 2-mercaptobenzothiazole, ferrocenium compounds or titanocenes, such as dicyclopentadienylbis(2,6-difluoro-3-pyrrolophenyl)titanium or borate photoinitiators or o-acyloxime photoinitiators, as described, for example, in GB 2339571.

Where the photoinitiators of the invention are employed in hybrid systems, i.e. systems which can be cured both free-radically and cationically, use is made, in addition to the free-radical curing agents of the formula Ia and/or Ib and any further free-radical curing agents, of cationic photoinitiators such as benzoyl peroxide (other suitable peroxides are described in U.S. Pat. No. 4,950,581, column 19; lines 17–25), aromatic sulfonium, phosphonium or iodonium salts, as described for example in U.S. Pat. No. 4,950,581, column 18, line 60 to column 19, line 10.

The photopolymerizable compositions contain the photoinitiator appropriately in an amount of from 0.05 to 15% by weight, preferably from 0.1 to 5% by weight, based on the composition. The stated amount of photoinitiator is based on the sum of all of the added photoinitiators, if mixtures thereof are used, i.e. both on the photoinitiator (B) and on the photoinitiators (B)+(E).

The photopolymerizable compositions may be used for a variety of purposes: for example, as a printing ink, as a clearcoat material, as a white paint, as a chromatically pigmented paint, for wood or metal, for example, as powder coating materials, as coating material for, inter alia, paper, wood, metal or plastic, as a daylight-curable coating for the marking of buildings and roads, for photographic reproduction techniques, for holographic recording materials, for image recording techniques or for producing printing plates which can be developed with organic solvents or using aqueous alkalis, for producing masks for screen printing, as dental filling compounds, as adhesives, including pressure-sensitive adhesives, as laminating resins, as etch resists or permanent resists, both liquid and in the form of dry films, as photostructurable dielectrics, and as solder resists for electronic circuits, as resists for producing colour filters for any type of screen, or for producing structures in the production process of plasma displays and electroluminescent displays, for the production of optical switches, optical lattices (interference grids), for the production of three-dimensional articles by mass curing (UV curing in transparent moulds) or by the stereolithography process, as described for example in U.S. Pat. No. 4,575,330, for producing composite materials (e.g. styrenic polyesters which may where appropriate contain glass fibres and/or other fibres and other auxiliaries), and of gel coats and high-film-build compositions, for the coating or sealing of electronic components, or as coatings for optical fibres. The compositions are suitable, furthermore, for the production of optical lenses, e.g. contact lenses or Fresnel lenses, and also for producing medical instruments, aids or implants.

The compositions may also be used to produce gels having thermotropic properties, as described for example in DE 19700064 and EP 678534.

The compounds of the formulae Ia, Ib may additionally be used as initiators for emulsion, bead or suspension polymerizations or as initiators in a polymerization for the fixing of states of order of liquid-crystalline monomers and oligomers, or as initiators for the fixing of dyes on organic materials.

The photocurable compositions of the invention are suitable, for example, as coating materials for substrates of all kinds, e.g. wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and Gas, Si or $SiO_2$, to which a protective coat or—by imagewise exposure—an Image is to be applied.

The photoinitiators according to present invention are also suitable for use in compositions as coatings for optical fibers. In general, optical fibers are coated with protective coats directly after their production. The fiber of glass is drawn and then one or more coatings are applied to the glass string. Usually, one, two or three coats are applied, the top coating, for example, is colored ("ink layer or ink coating"). Further, several thus coated optical fibers may be put together to a bundle and be coated all together, i.e. cabling of the fibers. The compositions according to the present invention in general are suitable for any of these coatings, which have to exhibit good softness over a broad temperature range, good tensile strength and toughness and rapid UV-curing characteristics.

Each of the coats, inner primary (usually a soft coating), outer primary or secondary (usually a harder coating than the inner coating), tertiary or the cabling coat, may comprise at least one radiation-curable oligomer, at least one radiation curable monomer diluent, at least one photoinitiator, and additives.

In general all radiation curable oligomers are suitable. Preferred are oligomers with a molecular weight of at least 500, for example 500–10,000, 700–10,000, 1,000–8,000 or 1,000–7,000, in particular urethane oligomers, containing at least one unsaturated group. Preferably the radiation curable oligomer has two terminal functional groups. The coat may contain not only one specific oligomer, but also mixtures of different oligomers. The preparation of suitable oligomers is known to the person skilled in the art and for example published in U.S. Pat. No. 6,136,880, incorporated herein by reference. The oligomers are, for example, prepared by reacting an oligomer diol, preferably a diol having 2–10 polyoxaalkylene groups, with a diisocyanate or a polyisocyanate and a hydroxy-functional ethylenically unsaturated monomer, e.g. hydroxyalkyl(meth)acrylate. Specific examples of each of the components named above, as well as suitable ratios of these components are given in U.S. Pat. No. 6,136,880, incorporated herein by reference.

The radiation curable monomer can be used in a manner to control the viscosity of the coating formulation. Accordingly, a low viscosity monomer with at least one functional group capable of photoinitiated polymerization is employed. The amount for example is chosen to adjust the viscosity in a range from 1,000 to 10,000 mPas, i.e. usually for example from 10–90, or 10–80 wt % are used. The functional group of the monomer diluent preferably is of the same kind than the one of the oligomer component, for example an acrylate or vinyl ether function and a higher alkyl or polyether moiety. Examples of monomer diluents suitable for coating compositions for optical fibers are published in U.S. Pat. No. 6,136,880, col. 12, line 11ff., incorporated herein by reference.

In primary coatings preferably monomers having an acrylate or vinyl ether functionality and a polyether moiety of 4 to 20 C atoms is used. Specific examples are given in the U.S. patent incorporated by reference and cited above.

The composition may also comprise a poly(siloxane) as described in U.S. Pat. No. 5,595,820 to improve the adhesive properties of the formulation on the optical fiber glass substrate. The coating composition usually also comprises further additives, e.g. antioxidants, light stabilizers, UV absorbers such as for example given in the list above in particular $^{RTM}$IRGANOX 1035, 1010, 1076, 1222, $^{RTM}$TINUVIN P, 234, 320, 326, 327, 328, 329, 213, 292, 144, 622LD (all provided by Ciba Specialty Chemicals), $^{RTM}$ANTIGENE P, 3C, FR, GA-80, $^{RTM}$SUMISORB TM-061 (provided by Sumitomo Chemical Industries Co.), $^{RTM}$SEESORB 102, 103, 501, 202, 712, 704 (provided by Sypro Chemical Co., Ltd.), $^{RTM}$SANOL LS770 (provided by Sankyo Co. Ltd.) to prevent the coloring of the coat, in particular during the processing, and to improve the stability of the cured coat. Particularly interesting are stabilizer combinations of hindered piperidine derivatives (HALS) and hindered phenol compounds, e.g. a combination of IRGANOX 1035 and TINUVIN 292, for example in a ratio of 1:1. Further, additives are for example wetting agents and other additives having an effect on the rheology properties of the coating. Also amines, for example diethylamine, can be added.

Other examples for additives for compositions for the coating of optical fibers are silane coupling agents, e.g. γ-aminopropyltriethoxysilane, γ-mercaptopropyltrimethoxysilane, γ-methacryloxypropyltrimethoxysilane, SH6062, SH6030 (provided by Toray-Dow Corning Silcone Co., Ltd.), KBE 903, KBE 603, KBE 403 (provided by Shin-Etsu Chemical Co., Ltd.)

In order to prevent coloring of the coatings the compositions may also comprise fluorescent additives or optical brighteners, as, for example, $^{RTM}$UVITEX OB, provided by Ciba Specialty Chemicals.

The photoinitiators according to the present application in coating compositions for optical fibers can be admixed with one or more other known photoinitiators. These are in particular monoacylphosphine oxides, such as diphenyl-2,4,6-trimethylbenzoyl phosphine oxide; bisacylphosphine oxides, such as bis(2,4,6-trimethylbenzoyl)-phenyl phosphine oxide ($^{RTM}$IRGACURE 819), bis(2,6-dimethoxybenzoyl)-2,4,4trimethylpentyl phosphine oxide; α-hydroxyketones, such as 1-hydroxycyclohexyl phenyl ketone ($^{RTM}$IRGACURE 184), 2-hydroxy-2-methyl-1-phenyl-1-propanone ($^{RTM}$DAROCUR 1173), 2-hydroxy-1-[4-(2-hydroxy-ethoxy)phenyl]-2-methyl-1-propanone ($^{RTM}$IRGACURE 2959); α-aminoketones, such as 2-methyl-1-[4-(methylthio)phenyl]-2-(4-morpholinyl)-1-propanone ($^{RTM}$IRGACURE 907), 2-benzyl-2-(dimethylamino)-1-[4-(4-morpholinyl)phenyl]-1-butanone ($^{RTM}$IRGACURE 369); benzophenones, such as benzophenone, 2,4,6-trimethylbenzophenone, 4-methylbenzophenone, 2-methylbenzophenone, 2-methoxycarbonylbenzophenone, 4,4'-bis(chloromethyl)benzophenone, 4-chlorobenzophenone, 4-phenylbenzophenone, 4,4'-bis(dimethylamino)benzophenone, 4,4'-bis(diethylamino)benzophenone, methyl 2-benzoylbenzoate, 3,3'-dimethyl-4-methoxybenzophenone, 4-(4-methylphenylthio)benzophenone and also ketal compounds, for example 2,2-dimethoxy-1,2-diphenyl-ethanone ($^{RTM}$IRGACURE 651); monomeric or dimeric phenylglyoxalic acid esters, such as for example methyl phenylglyoxalic acid ester or 1,2-(benzoylcarboxy)ethane. In particular suitable are admixtures with mono- or bisacyfphosphine oxides and/or α-hydroxy ketones.

It is evident that the formulations, in order to enhance the properties of the photoinitiators may also comprise sensitizer compounds, for example amines.

The coatings are either applied "wet on dry" or "wet on wet". In the first case after the application of the primary coat a curing step by irradiation with UV light is carried out prior to the application of the second coat. In the second case both coatings are applied and cured together by irradiation with UV light.

The curing with UV irradiation in this application usually takes place in a nitrogen atmosphere. In general all radiation sources usually employed in the photocuring technique can be used for the curing of optical fiber coatings. These are, for example the radiation sources listed below. Generally, mercury medium pressure lamps or/and Fusion D lamps are used. Also flash lights are suitable. It is evident that the emission of the lamps is matched with the absorption of the photoinitiator or photoinitiator mixture which is used. The optical fiber coating compositions may also be cured by irradiation with an electron beam, in particular with low power electron beams, as is, for example disclosed in WO 98/41484.

In order to distinguish different fibers in an assembly, the fibers may be covered with a third colored coating ("ink coating"). The compositions used for this coating in addition to the polymerizable components and the photoinitiator comprise a pigment or dye. Examples for pigments suitable for optical fiber coatings are inorganic pigments, such as for example titanium dioxide, zinc oxide, zinc sulfide, barium sulfate, aluminium silicate, calcium silicate, carbon black, black iron oxide, copper chromite black, iron oxides, chromium oxide greens, iron blue, chrome green, violet (e.g. manganese violet, cobalt phosphate, $CoLiPO_4$), lead chromates, lead molybdates, cadmium titanate and pearlescent and metallic pigments, as well as organic pigments, such as monoazo pigments, di-azo pigments, di-azo condensation pigments, quinacridone pigments, dioxazine violet, vat pigments, perylene pigments, thioindigo pigments, phthalocyanine pigments and tetrachloroisoindolinones. Examples for suitable pigments are carbon black for a black coating, titanium dioxide for a white coating, diarylide yellow or diazo based pigments for yellow coatings, phthalocyanine blue, and other phthalocyanines for blue coatings, anthraquinone red, naphthole red, monazo based pigments, quinacridone pigments, anthraquinone and perylenes for red coatings, phthalocyanine green and nitroso based pigments for green coatings, monazo and diazo based pigments, quinacridone pigments, anthraquinones and perylenes for orange coatings, and quinacridone violet, basic dye pigments and carbazole dioxazine based pigments for violet coatings. The person skilled in the art is well aware of formulating and combining suitable further pigments if even more colored coatings, such as aqua, brown, gray, pink etc. are needed.

The mean particle size of the pigments usually is about 1 µm or less. The size of commercial pigments can be reduced by milling, if necessary. The pigments for example, can be added to the formulation in the form of a dispersion in order to simplify the mixing with the other ingredients of the formulation. The pigments are, for example dispersed in a low viscosity liquid, e.g. a reactive diluent. Preferred is the use of organic pigments. Suitable amounts for pigment in the ink coating are for example 1–20, 1–15, preferably 1–10 wt %.

The ink coating in general also comprises a lubricant to provide improved break-out properties of the single coated optical fiber from the matrix. Examples of such lubricants are silicones, fluorocarbon oils or resins and the like, preferably a silicone oil or a functionalized silicone compound, e.g. silicone diacrylate is used.

The compositions according to the present invention are further suitable as a matrix material for an assembly of coated optical fibers. That is, several of the primary, secondary (and in some cases tertiary) coated fibers, for example, in the third coat being differentiated by different colors, are assembled in a matrix.

The coating of an assembly preferably besides the additives given above also contains a release agent to allow for easy access to the individual fibers during the installation of the optical fiber cables. I.e.

Examples for such release agents are teflon, silicones, silicon acrylates, fluorocarbon oils or resins and the like. The release agents suitably are added in an amount of 0.5–20 wt %. Examples of ink coatings and matrix materials for coated optical fibers are given in U.S. Pat. Nos. 6,197,422, 6,130, 980 and EP 614099, incorporated herein by reference.

The substrates may be coated by applying a liquid composition, a solution or suspension to the substrate. The choice of solvent and the concentration are guided primarily by the nature of the composition and by the coating technique. The solvent should be inert, i.e. it should not enter into any chemical reaction with the components and it should be able to be removed again in the course of drying after coating. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating techniques, for example by spin-coating, dipping, knife coating, curtain coating techniques, brush application, spraying, especially by electrostatic spraying, and reverse roll coating, and also by electrophoretic deposition. It is also possible to apply the photosensitive layer to a temporary flexible support and then, by layer transfer via lamination, to the final substrate.

Examples of those applications are described in Ullmann's Encyclopedia of Industrial Chemistry, 5. Ed., Vol.A18, pp. 491–500.

The application (coat thickness) and nature of the substrate (coat support) are dependent on the desired field of application. The dry film thickness range generally embraces values from about 0.1 µm to more than 100 µm, preferably from 0.02 to 2 cm.

A further field of use of photocuring is that of metal coating, as in the coating of metal sheets and tubes, cans or bottle closures, for example, and also photocuring on polymer coatings, for example PVC-based wall or floor coverings.

Examples of the photocuring of paper coatings are the colourless varnishing of labels, record sleeves or book covers.

Also preferred is the use of the coating formulation comprising the surface-active photoinitiators as a finishing paint for applications in the automobile industry, especially as a pigmented or unpigmented top coat of the coating, but use for layers beneath the top coat is also possible.

The photosensitivity of the compositions of the invention generally ranges from about 200 nm to about 600 nm (UV region). Suitable radiation is present, for example, in sunlight or light from artificial sources. Light sources employed therefore include a large number of a very wide variety of types. Both point sources and arrays (lamp carpets) are suitable. Examples are carbon arc lamps, xenon arc lamps, medium-, high- and low-pressure mercury lamps, possibly doped with metal halides (metal-halogen lamps), microwave-excited metal vapour lamps, excimer lamps, superactinic fluorescent tubes, fluorescent lamps, argon incandescent lamps, flashlights, photographic floodlamps, light-emitting diodes (LEDs), electron beams and X-rays. The distance between the lamp and the substrate to be exposed may vary depending on the intended application and the type and output of the lamps, for example between 2 cm and 150 cm.

Especially suitable are laser light sources, e.g. excimer lasers, such as Krypton-F lasers for exposure at 248 nm. Lasers in the visible range can also be used.

As already mentioned, curing in the process of the invention may take place solely by exposure to electromagnetic radiation. Depending on the composition of the formulation to be cured, however, thermal curing before, during or after radiation exposure is appropriate.

Thermal curing takes place in accordance with methods known to the person skilled in the art. Curing is generally carried out in an oven, e.g. a forced-air oven, on a hotplate, or by irradiation using IR lamps. Curing without auxiliaries at room temperature is likewise possible, depending on the binder system used. The curing temperatures are generally between room temperature and 150° C., e.g. 25–150° C. or 50–150° C. In the case of powder coating materials or coil coating materials, the curing temperatures may also be higher, e.g. up to 350° C.

Where the formulation includes thermally curable components (C), it is additionally possible in accordance with the invention to add thermal drying catalysts or curing catalysts to the formulation as additional additives (D). Examples of possible drying catalysts, or thermal curing catalysts, are organometallic compounds, amines and/or phosphines. Organometallic compounds are, for example, metal carboxylates, especially those of the metals Pb, Mn, Co, Zn, Hf, Zr or Cu, or metal chelates, especially those of metals Al, Ti, Hf or Zr, or organometallic compounds such as organotin compounds. Examples of metal carboxylates are the stearates of Pb, Mn or Zn, the octoates of Co, Zn or Cu, the naphthenates of Mn and Co or the corresponding linoleates or tallates. Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate and dibutyltin dioctoate. Examples of amines are, in particular, tertiary amines, such as tributylamine, triethanolamine, N-methyldiethanolamine, N-dimethylethanolamine, N-ethylmorpholine, N-methylmorpholine or diazabicyclooctane (triethylenediamine) and also the salts thereof. Further examples are quaternary ammonium salts, such as trimethylbenzylammonium chloride. As curing catalysts it is also possible to use phosphines, such as triphenylphosphine. Suitable catalysts are described, for example, as well in J. Bieleman, Lackadditive [Additives for Coatings], Wiley-VCH Verlag GmbH, Weinheim, 1998, page 244–247. Examples are sulfonic acids, such as p-toluenesulfonic acid, dodecylbenzenesulfonic acid, dinonylnaphthalenesulfonic acid or dinonylnaphthalenedisulfonic acid. For example, it is also possible to use latent or blocked sulfonic acids, where the blocking of the acid may be ionogenic or non-ionogenic.

Such catalysts are used in the concentrations known to the person skilled in the art and customary in that art.

The invention also provides a process for photopolymerizing non-volatile monomeric, oligomeric or polymeric compounds containing at least one ethylenically unsaturated double bond, which comprises exposing a composition as described above to electromagnetic radiation ranging from 200 nm into the IR region.

The invention additionally provides for the use of the above-described composition and to a process for producing pigmented and unpigmented paints and varnishes, powder coating materials, gel coats, composite materials or glass fibre cable coatings.

The invention likewise provides a coated substrate coated on at least one surface with a composition as described above.

The Examples which follow illustrate the invention, but do not indicate any intention that the invention be restricted to the examples. As in the remainder of the description and in the claims, parts and percentages are by weight unless indicated otherwise. References to alkyl radicals containing more than three carbon atoms without indication of the isomer should be understood in each case as referring to the n-isomers.

EXAMPLE A

Preparation of the Photoinitiator Entity

A.1: Preparation of Phenyl Isobutyrate

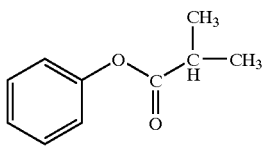

176.6 g of phenol are cooled to 5° C. under nitrogen in a flask fitted with thermometer, condenser and dropping funnel. In the course of 40 minutes, 250 g of isobutyl acid chloride are added and the solution is stirred at 5° C. for one hour. The temperature is increased to room temperature and stirring is continued for 2 hours. The mixture is distilled (b.p.=95–100° C. (20 mbar)) and 298 g of the pure product (97%) are obtained.

$^1$H-NMR (CDCl$_3$) δ [ppm]: 7.39 (m, 2H arom.); 7.22 (m, 1H arom.); 7.10 (m, 2H arom.); 3.54 (q×q, J=6.99, 1H); 1.33 (d, J=7.00, 6H, 2CH$_3$).

A.2: Preparation of 1-(4-hydroxyphenyl)-2-methyl-1-propanone

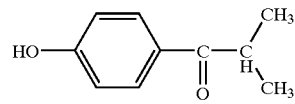

580.8 g of aluminium chloride are added at from 0 to 5° C., under nitrogen, to 1 liter of chlorobenzene in a flask fitted with thermometer, condenser and dropping funnel. The mixture is stirred at room temperature for 45 minutes. 298 g of the product prepared as described in A.1 are added dropwise in the course of 45 minutes, the temperature being maintained at from 20 to 25° C. The resulting suspension is stirred for 2 days at room temperature. The mixture is poured into a mixture of ice (3 kg) and hydrochloric acid (450 ml) and extracted with toluene. The organic phases are washed with brine. After drying over MgSO$_4$ and filtering, the solvent is removed in vacuo. 1 liter of water is added to the residue, and the pH value of the solution is increased to 14 using 30% sodium hydroxide solution, during which the temperature is maintained at 20° C. The resulting solution is extracted with ethyl acetate. The aqueous phase is cooled to 0° C. and the pH value is adjusted to 0 using concentrated hydrochloric acid, the organic phase is dried over MgSO$_4$ and filtered, and the solvent is removed in vacuo, yielding a liquid, which solidifies in the freezer. The pure product is obtained in the form of a white solid (213 g, 71%).

$^1$H-NMR (CDCl$_3$) δ [ppm]: 7.90 (m, 2H arom.); 6.94 (m, 2H arom.); 3.54 (q×q, J=6.84, 1H); 1.20 (d, J=6.82, 6H, 2CH$_3$).

A.3: Preparation of 2-hydroxy-1-(4-hydroxyphenyl)-2-methyl-1-propanone

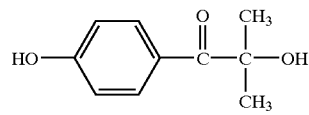

A solution of 213 g of the product prepared in A.2 in 475 ml of dioxane is cooled to 0° C. 228 g of bromine are added dropwise in the course of one hour, during which the temperature is maintained at from 10 to 15° C. The orange-coloured mixture is stirred for 2 hours at room temperature. The solution is poured into water (5.4 liters) and extracted with ethyl acetate. After drying the organic phases over MgSO$_4$ and filtration, the solvent is removed in vacuo, yielding a brown oil. 3 liters of water are added to the oil and the beige-coloured emulsion that forms is treated with 650 g of 30% sodium hydroxide solution. The mixture is stirred at room temperature for 3 hours. 293 ml of concentrated HCl are then added to adjust the pH value of the solution to 7. The resulting white suspension is stirred for 4 hours at 0° C. and overnight at room temperature. The mixture is then cooled to 5° C. and filtered. The crystals are washed with water and dried in vacuo at 40° C. First of all, 137.8 g are obtained in the form of dirty-white crystals. A further 47.8 g of a contaminated compound are obtained from the extracted mother liquor. Both products are purified in toluene and 135 g (58%) of pure product and 27 g (12%) of a product that is not entirely pure are isolated.

$^1$H-NMR (DMSOd$_6$) δ [ppm]: 10.23 (s, OH); 8.12 (m, 2H arom.); 6.79 (m, 2H arom.); 5.59 (s, OH); 1.37 (s, 6H, 2CH$_3$). Microanalysis: calc.: C, 66.65; H, 6.71; found: C, 65.60; H, 6.52.

EXAMPLE 1

2-Hydroxy-2-methyl-1-(4-octyloxy-phenyl)-1-propanone (1a) and 2-methyl-2-octyloxy-1-(4-octyloxy-phenyl)-1-propanone (1b)

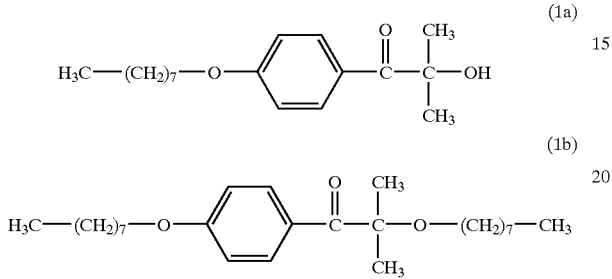

1a: Formula Ia, wherein R$_a$=formula IIa; R$_1$=R$_2$=R$_4$=R$_5$=H; R$_3$=—Y-A; R$_{11}$=R$_{12}$=—CH$_3$; X=—OR$_{20}$; R$_{20}$=H; Y=—O—; A=—(CH$_2$)$_7$—CH$_3$)

1b: Formula Ib, wherein R$_b$=formula IIb; R$_6$=R$_7$=R$_9$=R$_{10}$=H; R$_8$=—Y-A; R$_{11}$=R$_{12}$=—CH$_3$; X$_1$=—O—; Y=—O—; Y$_1$=a single bond; A=—(CH$_2$)$_7$—CH$_3$).

A solution of 2-hydroxy-1-(4-hydroxyphenyl)-2-methyl-1-propanone (10 g, 55.5 mmol) in dimethyl sulfoxide (DMSO) (125 ml) is added in the course of 1 hour at room temperature (RT), under argon, to a suspension of NaH (2.66 g, 61 mmol, 1.1 eq; 55–60% in oil, washed with hexane) in DMSO (40 ml). The mixture is stirred for 15 minutes at RT and for 15 minutes at from 35 to 40° C. A solution of 1-bromooctane (11.79 g, 61 mmol) in DMSO (10 ml) is added in the course of 15 minutes and the mixture is heated at 190° C. for 18 hours. The solution is poured onto ice and the resulting mixture is extracted with tert-butyl methyl ether (TBME). The organic phases are dried with MgSO$_4$. After filtration and removal of the solvent by evaporation, the compound is obtained in the form of an oil. Flash chromatography yields 2-hydroxy-2-methyl-1-(4-octyloxy-phenyl)-propan-1-one (13.9 g, 85%) in the form of a yellow oil and 2-methyl-2-octyloxy-1-(4-octyloxy-phenyl)-propan-1-one (1.1 g; 5%) in the form of a yellow oil.

1a: 2-Hydroxy-2-methyl-1-(4-octyloxy-phenyl)-propan-1-one

UV (CH$_3$CN) max. at 276 nm (ε 16,792). $^1$H-NMR (CDCl$_3$) δ [ppm]: 8.01 (d, 2H arom., J=9.0); 6.80 (d, 2H arom., J=9.3); 4.33 (s, OH); 4.00 (t, 2H, J=6.5, CH$_2$—O-Ph); 1.79 (m, H, CH$_2$—CH$_2$—O-Ph); 1.61 (s, 6H, 2CH$_3$); 1.50–1.20 (m, 10H, 5CH$_2$); 0.86 (m, 3H, CH$_3$).

1b: 2-Methyl-2-octyloxy-1-(4-octyloxy-phenyl)-propan-1-one

UV (CH$_3$CN) max. at 278 nm (ε 13,621). $^1$H-NMR (CDC$_{O3}$) δ [ppm]: 8.28 (d, 2H arom., J=7.0); 6.86 (d, 2H arom., J=7.0); 3.99 (t, 2H, J=6.5, CH$_2$—O-Ph); 3.24 (t, 2H, J=6.8, C(CH$_3$)$_2$—O—CH$_2$); 1.77 (m, 2H, CH$_2$—CH$_2$—O-Ph); 1.56–1.19 (m, 22H, 11CH$_2$); 1.48 (s, 6H, 2CH$_3$); 0.84 (m, 6H, 2CH$_3$).

EXAMPLE 2

1-(4-Dodecyloxy-phenyl)-2-hydroxy-2-methyl-1-propanone (2a) and 2-dodecyloxy-1-(4-dodecyloxy-phenyl)-2-methyl-1-propanone (2b)

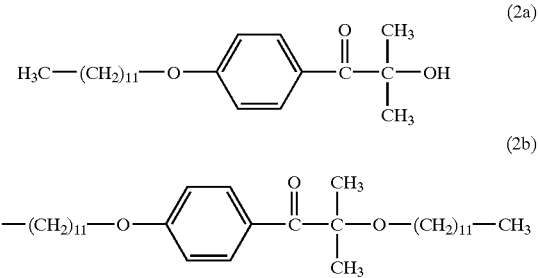

2a: Formula Ia, wherein R$_a$=formula IIa; R$_1$=R$_2$=R$_4$=R$_5$=H; R$_3$=—Y-A; R$_{11}$=R$_{12}$=—CH$_3$; X=—OR$_{20}$; R$_{20}$=H; Y=—O—; A=—(CH$_2$)$_{11}$—CH$_3$ 2b: formula Ib, wherein R$_b$=formula IIb; R$_6$=R$_7$=R$_9$=R$_{10}$=H; R$_8$=—Y-A; R$_{11}$=R$_{12}$=—CH$_3$; X$_1$=—O—; Y=—O—; Y$_1$=a single bond; A=—(CH$_2$)$_{11}$—CH$_3$ The compound of Example 2 is prepared according to the method described in Example 1, 1 mol equivalent of 2-hydroxy-1-(4-hydroxyphenyl)-2-methyl-1-propanone and 1.1 mol equivalents of 1-bromododecane being used.

2a: 1-(4-Dodecyloxy-phenyl)-2-hydroxy-2-methyl-propan-1-one $^1$H-NMR (CDCl$_3$) δ [ppm]: 8.04 (d, 2H arom., J=7.4); 6.93 (d, 2H, J=7.4); 4.34 (s, OH); 4.02 (t, 2H, J=5.4, CH$_2$—O-Ph); 1.80 (m, 2H, CH$_2$—CH$_2$—O-Ph); 1.63 (s, 6H, 2CH$_3$); 1.52–1.20 (m, 18H, 9CH$_2$); 0.88 (m, 3H, CH$_3$). Microanalysis: calc.: C, 75.82; H, 10.41; found: C, 75.84; H, 10.22.

2b: 2-Dodecyloxy-1-(4-dodecyloxy-phenyl)-2-methyl-propan-1-one

UV (CH$_3$CN) max. at 277 nm (ε 14,498). $^1$H-NMR (CDCl$_3$) δ [ppm]: 8.30 (d, 2H arom., J=7.4); 6.88 (d, 2H arom., J=7.4); 4.01 (t, 2H, J=5.3, CH$_2$—O-Ph); 3.25 (t, 2H, J=5.6, C(CH$_3$)$_2$—O—CH$_2$); 1.80 (m, 2H, CH$_2$—CH$_2$—O-Ph); 1.60–1.12 (m, 38H, 19CH$_2$); 1.50 (s, 6H, 2CH$_3$); 0.88 (m, 6H, 2CH$_3$). Microanalysis: calc.: C, 79.01; H, 11.70; found: C, 78.91; H, 11.58.

EXAMPLE 3

2-Hydroxy-2-methyl-1-(4-octadecyloxy-phenyl)-1-propanone (3a) and 2-methyl-2-octadecyloxy-1-(4-octadecyloxy-phenyl)-1-propanone (3b)

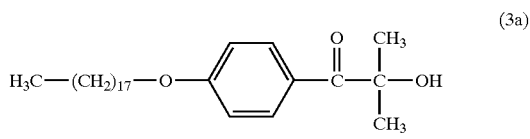

-continued

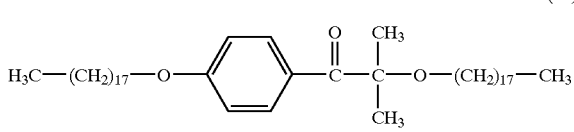
(3b)

3a: Formula Ia, wherein $R_a$=formula IIa; $R_1=R_2=R_4=R_5$=H; $R_3$=—Y-A; $R_{11}=R_{12}$=—CH$_3$; X=—OR$_{20}$; R$_{20}$=H; Y=—O—; A=—(CH$_2$)$_{17}$—CH$_3$ 3b: Formula Ib, wherein $R_b$=formula IIb; $R_6=R_7=R_9=R_{10}$=H; $R_8$=—Y-A; $R_{11}=R_{12}$=—CH$_3$; $X_1$=—O—; Y=—O—; $Y_1$=a single bond; A=—(CH$_2$)$_{17}$—CH$_3$ The compound of Example 3 is prepared in accordance with the method described in Example 1, 1 mol equivalent of 2-hydroxy-1-(4-hydroxyphenyl)-2-methyl-1-propanone and 1.1 mol equivalents of 1-bromooctodecane being used.

3a: 2-Hydroxy-2-methyl-1-(4-octadecyloxy-phenyl)-propan-1-one

UV (CH$_3$CN) max. at 283 nm ($\epsilon$ 16,709). $^1$H-NMR (CDC$_{13}$) $\delta$ [ppm]: 7.85 (m, 2H arom.); 6.73 (m, 2H arom.); 3.84 (m, 2H, CH$_2$—O-Ph); 1.60 (m, 2H, C$\underline{H}_2$—CH$_2$—O-Ph); 1.44 (s, 6H, CH$_2$); 1.32–0.95 (m, 30H, 15CH$_2$); 0.68 (m, 3H, CH$_3$). m/z (CI): 433 (MH$^+$). Microanalysis: calc.: C, 7.73; H, 11.18; found: C, 77.42; H, 11.10.

3b: 2-Methyl-2-octadecyloxy-1-(4-octadecyloxy-phenyl)-propan-1-one

UV (CH$_3$CN) max. at 280 nm ($\epsilon$ 15,432). $^1$H-NMR (CDCl$_3$) $\delta$ [ppm]: 8.22 (d, 2H arom., J=9); 6.82 (d, 2H arom., J=9); 3.94 (t, 2H, J=6.6, CH$_2$—O-Ph); 3.19 (t, 2H, J=6.8, C(CH$_3$)$_2$—O—C$\underline{H}_2$); 1.71 (m, 2H, C$\underline{H}_2$—CH$_2$—O-Ph); 1.43 (s, 6H, 2CH$_3$); 1.40 (s, 2H, CH$_2$); 1.32–1.10 (m, 60H, 30CH$_2$); 0.81 (m, 6H, 2CH$_3$). m/z (CI): 685 (MH$^+$). Microanalysis: calc.: C, 80.64; H, 12.36; found: C, 80.33; H, 12.32.

EXAMPLE 4

1-(4-Docosyloxy-phenyl)-2-hydroxy-2-methyl-1-propanone

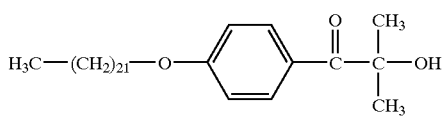

Formula Ia, wherein $R_a$=formula IIa; $R_1=R_2=R_4=R_5$=H; $R_3$=—Y-A; $R_{11}=R_{12}$=—CH$_3$; X=—OR$_{20}$; $R_{20}$=H; Y=—O—; A=—(CH$_2$)$_{21}$—CH$_3$ A solution of 2-hydroxy-1-(4-hydroxyphenyl)-2-methyl-1-propanone (5.65 g, 31 mmol), 1-bromodocosane (13.43 g, 34 mmol) and potassium carbonate (4.76 g, 34 mmol) in acetone (100 ml) is stirred for 25 hours under N$_2$ at 57° C. The mixture is poured into toluene (250 ml) and water (250 ml). The phases are separated and the water is extracted with toluene. The organic phases are dried over MgSO$_4$. After removal of the solvent by evaporation, the compound is obtained in quantitative yield in the form of a beige solid.

M.p.=64–65.5° C. UV (CH$_3$CN) max. at 282 nm ($\epsilon$ 14,121). $^1$H-NMR (CDCl$_3$) $\delta$ [ppm]: 8.08 (m, 2H arom.); 6.97 (m, 2H arom.); 4.07 (m, 2H, CH$_2$—O-Ph); 1.85 (m, 2H, C$\underline{H}_2$—CH$_2$—O-Ph); 1.46 (m, 2H, C$\underline{H}_2$—CH$_2$—CH$_2$—O-Ph); 1.29 (m, 42H, 2CH$_3$ and 18CH$_2$); 0.91 (m, 3H, CH$_3$).

EXAMPLE 5

2-Methyl-2-octyloxy-1-[4-(2-octyloxy-ethoxy)-phenyl]-1-propanone

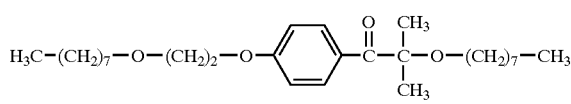

Formula Ib, wherein $R_b$=formula IIb; $R_6=R_7=R_9=R_{10}$=H; $R_8$=—Y-A; $R_{11}=R_{12}$=—CH$_3$; $X_1$=—O—; Y=—O—(CH$_2$)$_a$—O—; a=2; $Y_1$=a single bond; A=—(CH$_2$)$_7$CH$_3$ The compound of Example 5 is prepared in accordance with the method described in Example 1, 1 mol equivalent of 2-hydroxy-1-[4-(2-hydroxy-ethoxy)-phenyl]-2-methyl-1-propanone and 1.1 mol equivalents of 1-bromooctane being used.

$^1$H-NMR (CDCl$_3$) $\delta$ [ppm]: 8.23 (d, 2H arom., J=9.3); 6.84 (d, 2H arom., J=9.3); 4.10 (m, 2H, CH$_2$—O-Ph); 3.72 (m, 2H, C$\underline{H}_2$—CH$_2$—O-Ph); 3.44 (m, 2H, CH$_2$—O); 3.18 (m, 2H, CH$_2$—O); 1.46 (m, 2H, CH$_2$); 1.40 (m, 2H, CH$_2$); 1.38 (s, 6H, 2CH$_3$); 1.30–1.05 (m, 20H, 10CH$_2$); 0.78 (m, 6H, 2CH$_3$). IR (KBr film, cm$^{-1}$): 2928; 2856; 1672 (CO); 1600. Microanalysis: calc.: C, 74.95; H, 10.78; found: C, 74.92; H, 10.75.

EXAMPLE 6

1-[4-(2-Dodecyloxy-ethoxy)-phenyl]-2-hydroxy-2-methyl-1-propanone

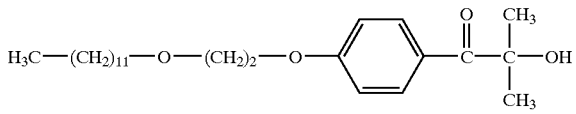

Formula Ia, with $R_a$=formula IIa; $R_1=R_2=R_4=R_5$=H; $R_3$=—Y-A; $R_{11}=R_{12}$=—CH$_3$; X=—OR$_{20}$; $R_{20}$=H; Y=—O—(CH$_2$)$_a$—O—; a=2; A=(CH$_2$)$_{11}$—CH$_3$ The compound of Example 6 is prepared in accordance with the method described in Example 1, 1 mol equivalent of 2-hydroxy-1-[4-(2-hydroxy-ethoxy)-phenyl]-2-methyl-1-propanone and 1.1 mol equivalents of 1-bromododecane being used.

UV (CH$_3$CN) max. at 273 nm ($\epsilon$ 15,986). $^1$H-NMR (CDCl$_3$) $\delta$ [ppm]: 7.98 (m, 2H arom.); 6.89 (d, 2H arom.); 4.12 (m, 2H, CH$_2$—O-Ph); 3.73 (m, 2H, C$\underline{H}_2$—CH$_2$—O-Ph); 3.43 (m, 2H, CH$_2$—O); 1.56 (m, s, 6H, 2CH$_3$); 1.53 (m, 2H, CH$_2$); 1.51 (m, 18H, 9CH$_2$); 0.81 (m, 3H, CH$_3$). m/z (CI): 393 (MH$^+$). Microanalysis: calc.: C, 73.43; H, 10.27; found: C, 73.49; H, 10.34.

EXAMPLE 7

2-Hydroxy-2-methyl-1-[4-(2-octadecyloxy-ethoxy)-phenyl]-1-propanone

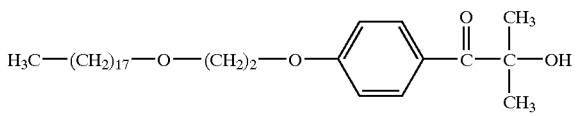

Formula Ia, wherein $R_a$=formula IIa; $R_1=R_2=R_4=R_5=$H; $R_3=$—Y-A; $R_{11}=R_{12}=$—$CH_3$; X=—$OR_{20}$; $R_{20}=$H; Y=—O—$(CH_2)_a$—O—; a=2; A=—$(CH_2)_{17}$—$CH_3$ The compound of Example 7 is prepared in accordance with the method described in Example 1, 1 mol equivalent of 2-hydroxy-1-[4-(2-hydroxy-ethoxy)-phenyl]-2-methyl-1-propanone and 1.1 mol equivalents of 1-bromooctodecane being used.

UV ($CH_3CN$) max. at 279 nm ($\epsilon$ 16,203). $^1$H-NMR ($CDCl_3$) $\delta$ [ppm]: 8.19 (m, 2H arom.); 7.10 (m, 2H arom.); 4.33 (m, 2H, $CH_2$—O-Ph); 3.94 (m, 2H, C$H_2$—$CH_2$—O-Ph); 3.65 (m, 2H, $CH_2$—O); 1.77 (s, 6H, 2$CH_3$); 1.71 (m, 2H, $CH_2$); 1.39 (m, 30H, 15$CH_2$); 1.02 (m, 3H, $CH_3$). Microanalysis: calc.: C, 75.58; H, 10.99; found: C, 75.56; H, 10.23.

EXAMPLE 8

A Clear UV-curable System Based on Polyurethane Acrylate is Prepared by Mixing

| | |
|---|---|
| 50 parts | Actitan ® 200, difunctional urethane acrylate (Akcros) |
| 25 parts | SR 306, tripropylene glycol diacrylate (Cray Valley) |
| 15 parts | TMPTA, trimethylolpropane triacrylate (UCB) |
| 10 parts | SR 399, dipentaerythritol pentaacrylate (Cray Valley) |

The samples were prepared by adding 2% of photoinitiator.

The mixtures were applied to a white chip board, irradiated by using a UV-processor (2×80 W/cm) at a belt speed of 3 m/min. A tack free dry film with a thickness of approximately 50 μm is obtained.

30 Minutes after cure, the pendulum hardness according to König (DIN 53157) is measured. Surface energy of the coating Is determined by measuring static water contact angle (θ) using a contact angle measuring system G10 from Krüss. The higher the values of the pendulum hardness measurement, the harder is the cured surface. The higher the contact angle, the better is the moisture resistance and scratch resistance.

| Initiator/light stabilizer used | pendulum hardness [sec] | water contact angle θ |
|---|---|---|
| 2% Darocur ® 1173 | 147 | 64 |
| 2% Ex. 2b | 150 | 83 |
| 2% Ex. 1a | 168 | 74 |
| 2% Ex. 2a | 155 | 74 |
| 2% Ex. 3a | 151 | 72 |
| 2% Ex. 4 | 160 | 81 |
| 2% Ex. 6 | 149 | 74 |

EXAMPLE 9

A Clear Dual-Cure-System Based on Polyurethenes is Prepared by Mixing

| | |
|---|---|
| 21.1 parts | Desmophen ® LS 2009/1, hydroxy functional polyacrylate, (Bayer AG) parts Roskydal ® FWO 2518C, isocyanurate based urethane acrylate, 80% |
| 32.3 | in butyl acetate (Bayer AG) parts Baysilone ® OL 17, flow improver, 10% in Xylene (Bayer AG) |
| 0.3 parts | Modaflow ®, flow improver (Monsanto) |
| 0.3 parts | 1-methoxy-2-propanol, (Fluka Chemicals) |
| 26.0 parts | Byk ® 306, flow improver (Byk-Chemie) |
| 0.5 parts | Roskydal ® FWO 2545 E, urethane acrylate with isocyanate groups |
| 11.2 | (Bayer AG) |

The samples were prepared by adding 2% of photoinitiator.

The mixtures were applied to a white coil-coat aluminum, air-dried for 5 minutes at room temperature and heated on a hot plate at 80° C. for 10 minutes. Irradiation is then carried out using a UV-processor (2×120 W/cm) at a belt speed of 5 m/min. A tack free dry film with a thickness of approximately 40 μm is obtained.

45 Minutes after cure, the pendulum hardness according to König (DIN 53157) is measured. Surface energy of the coating is determined by measuring static water contact angle (θ) using a contact angle measuring system G10 from Krüss. The higher the values of the pendulum hardness measurement, the harder is the cured surface. The higher the contact angle, the better is the moisture resistance and scratch resistance.

| Initiator | pendulum hardness [sec] | water contact angle θ |
|---|---|---|
| 2% Darocur 1173 | 85 | 81 |
| 2% Ex. 2b | 85 | 89 |
| 2% Ex. 1b | 88 | 88 |
| 2% Ex. 2a | 94 | 87 |
| 2% Ex. 3a | 91 | 87 |
| 2% Ex. 4 | 92 | 88 |
| 2% Ex. 6 | 92 | 87 |

The invention claimed is:

1. A process for the production of a coating having a scratch-resistant durable surface, which comprises
   (1) preparing a photocurable formulation comprising
      (A) an ethylenically unsaturated polymerizable compound; and
      (B) a photoinitiator;
   (2) applying the formulation to a substrate; and
   (3) curing the formulation either solely by irradiation with electromagnetic radiation, or by irradiation with electromagnetic radiation and the simultaneous and/or subsequent action of heat;

wherein the formulation comprises as photoinitiator (B) at least one surface-active photoinitiator, concentrated at the surface of the formulation, and selected from the group consisting of

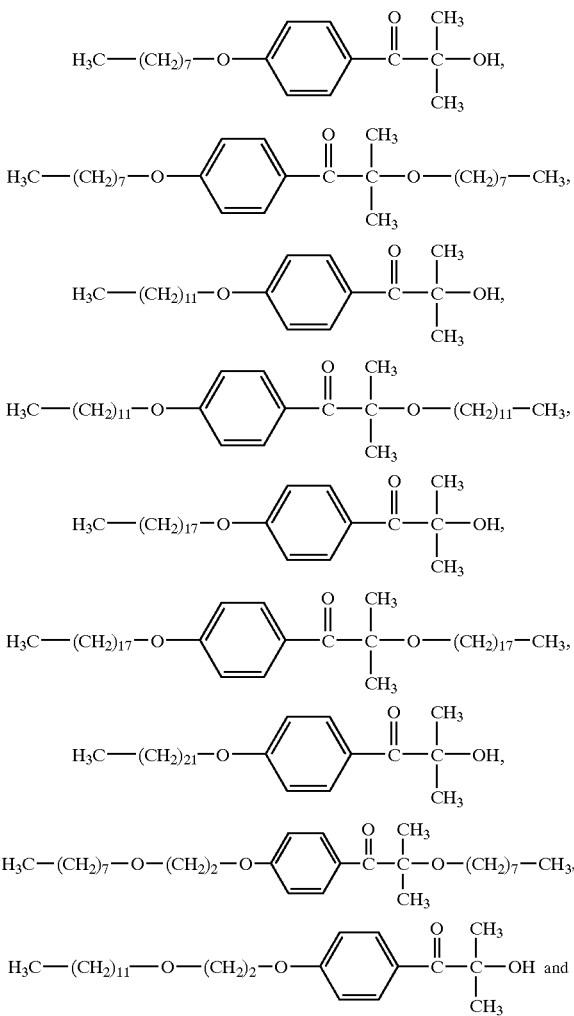

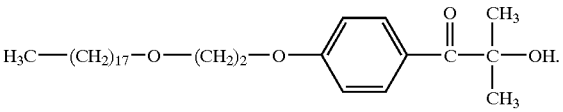

2. A process according to claim 1, wherein the photoinitiator (B) is

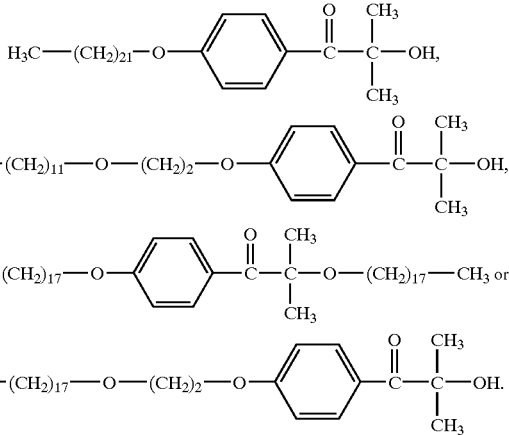

3. A process according to claim 1, wherein the photocurable formulation comprises as further component at least one thermally crosslinkable compound (C), and the formulation is cured by irradiation with electromagnetic radiation of a wavelength ranging from 200 to 600 nm and the simultaneous and/or subsequent action of heat.

4. A process according to claim 3, wherein the thermally crosslinkable compound (C) is a binder based on a polyacrylate with melamine or on a melamine derivative, or is a system based on a polyacrylate polyol or/and polyester polyol with an unblocked polyisocyanate or polyisocyanurate.

5. A process according to claim 1 for the preparation of pigmented and unpigmented surface coatings, powder coatings, thin layer gel coats, composites or coatings for glass fibre cables.

* * * * *